United States Patent
Ochi et al.

(10) Patent No.: US 10,696,948 B2
(45) Date of Patent: Jun. 30, 2020

(54) METHOD FOR PREPARING PLURIPOTENT STEM CELL-DERIVED CARDIOMYOCYTE POPULATION

(71) Applicant: OSAKA UNIVERSITY, Osaka (JP)

(72) Inventors: Yukiko Ochi, Osaka (JP); Kiyotoshi Sekiguchi, Osaka (JP); Shigeru Miyagawa, Osaka (JP); Yoshiki Sawa, Osaka (JP); Antti Markus Siltanen, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 494 days.

(21) Appl. No.: 15/511,275

(22) PCT Filed: Sep. 14, 2015

(86) PCT No.: PCT/JP2015/076072
§ 371 (c)(1),
(2) Date: Mar. 15, 2017

(87) PCT Pub. No.: WO2016/043168
PCT Pub. Date: Mar. 24, 2016

(65) Prior Publication Data
US 2019/0153391 A1 May 23, 2019

(30) Foreign Application Priority Data
Sep. 16, 2014 (JP) ................. 2014-188180

(51) Int. Cl.
*C12N 5/077* (2010.01)
*A61K 35/34* (2015.01)
*C12N 5/074* (2010.01)

(52) U.S. Cl.
CPC ............ *C12N 5/0657* (2013.01); *A61K 35/34* (2013.01); *C12N 5/0696* (2013.01); *C12N 2506/45* (2013.01); *C12N 2533/52* (2013.01)

(58) Field of Classification Search
CPC ................ C12N 5/0657; C12N 5/0696; C12N 2506/45; C12N 2533/52; A61K 35/34
See application file for complete search history.

(56) References Cited

U.S. PATENT DOCUMENTS

| 2003/0219889 | A1 | 11/2003 | Sumaru et al. |
| 2007/0010012 | A1 | 1/2007 | Gold et al. |
| 2009/0246182 | A1* | 10/2009 | Casteilla ............... C12N 5/0657 424/93.21 |
| 2009/0275132 | A1 | 11/2009 | Hattori et al. |
| 2011/0306086 | A1 | 12/2011 | Nitta |
| 2012/0220031 | A1 | 8/2012 | Sekiguchi et al. |
| 2013/0252335 | A1 | 9/2013 | Kume et al. |
| 2013/0330825 | A1 | 12/2013 | Couture et al. |
| 2014/0057287 | A1 | 2/2014 | Yamashita et al. |
| 2014/0127806 | A1 | 5/2014 | Sekiguchi et al. |
| 2015/0184129 | A1 | 7/2015 | Yamanaka et al. |
| 2015/0284684 | A1 | 10/2015 | Gold et al. |

FOREIGN PATENT DOCUMENTS

| JP | 2003-339373 | 12/2003 |
| JP | 2008-543338 | 12/2008 |
| JP | 2010-207133 | 9/2010 |
| JP | 2011-78370 | 4/2011 |
| JP | 2012-100625 | 5/2012 |
| JP | 2013-143968 | 7/2013 |
| JP | 2014-511139 | 5/2014 |
| WO | 2011/043405 | 4/2011 |
| WO | 2012/056997 | 5/2012 |
| WO | 2012/137970 | 10/2012 |
| WO | 2012/147992 | 11/2012 |
| WO | 2014/014119 | 1/2014 |
| WO | 2015/004539 | 1/2015 |

OTHER PUBLICATIONS

Miyazaki et al. "Laminin E8 fragments support efficient adhesion and expansion of dissociated human pluripotent stem cells." Nat Commun. 2012;3:1236. (Year: 2012).*
Polejaeva et al. "Stem cell potency and the ability to contribute to chimeric organisms." Reproduction. Mar. 7, 2013;145(3):R81-8 (Year: 2013).*
Brevini et al. "Porcine embryonic stem cells: Facts, challenges and hopes." Theriogenology. Sep. 1, 2007;68 Suppl 1:S206-13. Epub Jun. 19, 2007. (Year: 2007).*
Lavial et al. "Chicken embryonic stem cells as a non-mammalian embryonic stem cell model." Dev Growth Differ. Jan. 2010;52(1): 101-14. (Year: 2010).*
Ma et al. "Bioinformatic analysis of the four transcription factors used to induce pluripotent stem cells." Cytotechnology. Dec. 2014; 66(6): 967-978. (Year: 2014).*
International Search Report dated Dec. 15, 2015 in International Application No. PCT/JP2015/076072.
International Preliminary Report on Patentability dated Dec. 15, 2015 in International Application No. PCT/JP2015/076072.

(Continued)

*Primary Examiner* — Titilayo Moloye
(74) *Attorney, Agent, or Firm* — Wenderoth, Lind & Ponack, L.L.P.

(57) ABSTRACT

The present invention provides a method for preparing a clinically applicable, safe and less damaged cardiomyocyte population through a brief and simple procedure from a cell population obtained by induced differentiation of pluripotent stem cells into cardiomyocytes. The present invention relates to a method for preparing a cardiomyocyte population, the method comprising the steps of:

(1) inducing pluripotent stem cells to differentiate into cardiomyocytes, (2) bringing a cell population obtained by the induced differentiation into contact with a laminin selected from the group consisting of laminin α2β1γ1, laminin α2β2γ1, laminin α1β1γ1 and laminin α1β2γ1, or a fragment thereof having integrin binding activity, and (3) retrieving cells adherent to the laminin or the laminin fragment.

4 Claims, 9 Drawing Sheets

(56) References Cited

OTHER PUBLICATIONS

Ziober, B.L., et al., "Alternative Extracellular and Cytoplasmic Domains of the Integrin α7 Subunit Are Differentially Expressed During Development", J. Biol. Chem., 1993, 268(35), pp. 26773-26783.

Leung, E., et al., "A Novel Extracellular Domain Variant of the Human Integrin α7 Subunit Generated by Alternative Intron Splicing[1]", Biochem. Biophys. Res. Commun., 1998, 243, pp. 317-325.

Maitra, N., et al., "Expression of α & β integrins during terminal differentiation of cardiomyocytes", Cardiovascular Research, 2000, 47, pp. 715-725.

Von der Mark, H., et al., "Alternative Splice Variants of $α_7 β_1$ Integrin Selectively Recognize Different Laminin Isoforms", J. Biol. Chem., 2002, 277(8), pp. 6012-6016.

Ryoko Nishiuchi et al., "Saibo Secchaku Inshi no Seibutsugaku", Tissue Engineering 2007, 1st edition, 1st print, Nihon-Igakukan Co,. Ltd., Jun. 27, 2007, pp. 88-95, with partial English translation.

Nishiuchi R., et al., "Ligand-binding specificities of laminin-binding integrins: A comprehensive survey of laminin-integrin interactions using recombinant α3β1, α6β1, α7β1, and α6β4, integrins", Matrix Biology, 2006, 25, pp. 189-197.

Taniguchi, Y., et al., "The C-terminal Region of Laminin β Chains Modulates the Integrin Binding Affinities of Laminins", J. Biol. Chem, Mar. 20, 2009, 284(12), pp. 7820-7831.

Miyazaki T., et al., "Recombinant human laminin isoforms can support the undifferentiated growth of human embryonic stem cells", Biochem. Biophys. Res. Commun, 2008, 375, pp. 27-32.

Singh, A., et al., "Adhesion strength-based, label-free isolation of human pluripotent stem cells", Nature Methods, 2013, 10(5), pp. 438-444.

Lee, S.T., et al., "Development of three dimensional culture and expression of integrin heterodimers in human embryonic stem cells", Organogenesis, 2013, 9(3), pp. 143-148.

Yukiko Imanishi et al., "Examination of Purification Method of Human iPS-derived Cardiomyocytes Using Laminins, Regenerative Medicine", Feb. 1, 2015, 14(suppl.), p. 355, with partial English translation.

Yang L., et al., "Human cardiovascular progenitor cells develop from a KDR[+] embryonic-stem-cell-derived population", Nature, vol. 453, May 22, 2008, pp. 524-528.

Takahashi K., et al., "Induction of Pluripotent Stem Cells from Adult Human Fibroblasts by Defined Factors", Cell, 131, Nov. 30, 2007, pp. 861-872.

Kawamura M., et al., "Feasibility, Safety, and Therapeutic Efficacy of Human Induced Pluripotent Stem Cell-Derived Cardiomyocyte Sheets in a Porcine Ischemic Cardiomyopathy Model", Circulation, Sep. 11, 2012, pp. S29-S37.

Thavandiran N., et al., "Design and formulation of functional pluripotent stem cell-derived cardiac microtissues", Proc Natl Acad Sci U.S.A., Nov. 18, 2013, E4698-E4707.

Yu T., et al., "In Vivo Differentiation of Induced Pluripotent Stem Cell-Derived Cardiomyocytes", Circulation Journal, vol. 77, May 2013, pp. 1297-1306.

Extended European Search Report dated Feb. 7, 2018 in corresponding European patent application No. 15841142.1.

Ting et al., "Differentiation of Human Embryonic Stem Cells to Cardiomyocytes on Microcarrier Cultures", Current Protocols in Stem Cell Biology, 2012, Supplement 21, pp. 1D.7.1-1D.7.14 (14 pages).

Burridge et al., "Chemically defined generation of human cardiomyocytes", Nature Methods, 2014, vol. 11, No. 8, pp. 855-860.

Koch-Schneidemann et al., "Attachment of Adult Rat Cardiomyocytes (ARC) on Laminin and Two Laminin Fragments", Journal of Structural Biology, 1994, vol. 113, No. 2, pp. 107-116.

\* cited by examiner

METHOD FOR PREPARING PLURIPOTENT STEM CELL-DERIVED CARDIOMYOCYTE POPULATION

TECHNICAL FIELD

The present invention relates to a method for preparing a pluripotent stem cell-derived cardiomyocyte population.

BACKGROUND ART

Various methods have been reported for induced differentiation of human pluripotent stem cells into cardiomyocytes and include, for example, a method in which human pluripotent stem cells maintained on feeder cells are differentiated with activin A and BMP4 (bone morphogenetic protein 4) (Non Patent Literature 1 and 2), a method in which human pluripotent stem, cells maintained on Matrigel are differentiated with Wnt3a, R-Spondin-1 and DKK1 (Non Patent Literature 3), and a method in which human pluripotent stem cells maintained on feeder cells are differentiated on a large scale in a bioreactor (Non Patent Literature 3).

When pluripotent stem cells are induced to differentiate into cardiomyocytes, the differentiation efficiency usually varies from lot to lot. In the case where such cardiomyocytes are used as a cell source for transplantation in regenerative medicine, if not meeting the purity criteria, they need to be purified. The ideal purity of human pluripotent stem cell-derived cardiomyocytes for use in regenerative medicine is not necessarily 100%, and in fact, about 70% purity is better from a functional perspective according to the previous report (Non Patent Literature 4). Therefore, if human pluripotent stem cell-derived cardiomyocytes with a purity of less than 70% can be enriched, to a purity of about 70%, it will be of great significance in particular in the preparation of a cell source for transplantation in cell therapy. In addition, since it is difficult to achieve the same level of the efficiency of cardiomyocyte differentiation in every lot, the differences in the efficiency among lots probably affect the reproducibility of the results in new drug screening studies. Moreover, sensitive detection of the drug response of cardiomyocytes requires the minimization of the background noise from the cells other than cardiomyocytes.

Several methods have already been reported for the increase of the purity of cardiomyocytes after induced differentiation. These methods can be roughly classified into two categories. The methods in the first category utilize the cell's auxotrophy to eliminate cells other than cardiomyocytes. That is, they are methods in which a medium deprived of nutrients essential for the survival of cells other than cardiomyocytes is used for culture to eliminate these cells. For example, Patent Literature 1 describes a method for increasing the purity of cardiomyocytes, the method comprising using a medium with a low glucose concentration. However, this method causes great damage to cardiomyocytes in addition to other cells, which is matter of concern. Another problem is that the selection of cardiomyocytes requires a prolonged time (at least a few days).

The methods in the second category utilize antibodies against cardiomyocyte-specific surface antigens or glycans to isolate cardiomyocytes. That is, they are methods using flow cytometry or magnetic beads. However, disadvantageously, in the case of using flow cytometry, the time required for cell isolation significantly increases in accordance with the increase in the required amount of the cells. In addition, the use of flow cytometry and magnetic beads cause a concern about the damage and contamination of the retrieved, cells. Therefore, it is not realistic to employ these methods in the case requiring a large quantity of cells, for example, in the case of cell transplantation. Moreover, in these methods, the examination of whether or not residual antibodies or magnetic beads are present is essential and takes time and effort. If residual magnetic beads are detected in the isolated cells, the safety of the cells for transplantation is difficult to guarantee.

An ideal method for preparing cells to be used for transplantation through the purification of differentiated cells derived from human pluripotent stem cells needs to meet the following requirements: the purity and yield of differentiated cells is high; the safety for human recipients is guaranteed; and the prepared cells are capable of performing the desired functions in vivo after transplantation. More ideally, the preparation method can handle a large quantity of cells in a short period of time in a simple manner with causing less damage to the cells. However, in reality, previously reported methods are unsatisfactory for the preparation of clinically applicable cells. Therefore, strongly desired is the development of a novel method for preparing a large quantity of clinically applicable cells, i.e., safe and less damaged cells, in a simple manner.

CITATION LIST

Patent Literature

Patent Literature 1: JP-A 2013-143968

Non Patent Literature

Non Patent Literature 1:
Yang L et al., Nature, 2008 May 22; 453(7194): 524-8, doi; 10.1038/nature06894, Epub 2008 Apr. 23
Non Patent Literature 2:
Takahashi K et al., Cell, 2007 Nov. 30; 131(5): 861-72
Non Patent Literature 3:
Kawamura M et al., Circulation, 2012 Sep. 11; 126 (11 Suppl 1): S29-37
Non Patent Literature 4:
Thavandiran N et al., Proc Natl Acad Sci USA 2013 Dec. 3; 110(49): E4698-707, doi: 10.1073/pnas.1311120110, Epub 2013 Nov. 19

SUMMARY OF INVENTION

Technical Problem

An object of the present invention is to provide a method for preparing a clinically applicable, safe and less damaged cardiomyocyte population through a brief and simple procedure from a cell population obtained by induced differentiation of pluripotent stem cells into cardiomyocytes.

Solution to Problem

The present invention includes the following to achieve the above-mentioned object.
[1] A method for preparing a cardiomyocyte population, comprising the steps of:
(1) inducing pluripotent stem cells to differentiate into cardiomyocytes,
(2) bringing a cell population obtained by the induced differentiation into contact with a laminin selected from the group consisting of laminin α2β1γ1, laminin α2β2γ1, laminin α1β1γ1 and laminin α1β2γ1, or a fragment thereof having integrin binding activity, and
(3) retrieving cells adherent to the laminin or the laminin fragment.
[2] The method according to the above [1], further comprising a step of eliminating undifferentiated cells from a cell population obtained by the induced differentiation.
[3] The method according to the above [2], wherein the step of eliminating undifferentiated cells is performed between steps (1) and (2) and comprises the substeps of:
(A) bringing the cell population obtained by the induced differentiation into contact with a laminin selected from the group consisting of laminin α5β1γ1, laminin α5β2γ1, laminin α3β1γ1, laminin α3β2γ1 and laminin α3β3γ2, or a fragment thereof having integrin binding activity, and
(B) retrieving cells not adherent to the laminin or the laminin fragment.
[4] The method according to any one of the above [1] to [3], wherein, the contact of the cell population with the laminin or a fragment thereof having integrin binding activity in step (2) and/or substep (A) is achieved using a culture vessel having a culture surface coated with the laminin or the laminin fragment, or a carrier coated with the laminin or the laminin fragment.
[5] The method according to any one of the above [1] to [4], wherein the laminin fragment having integrin binding activity is a laminin E8 fragment.
[6] The method according to the above [5], wherein the laminin E8 fragment is used at a coating concentration of 0.1 μg/cm$^2$ to 2 μg/cm$^2$.
[7] The method according to the above [5] or [6], wherein the contact in step (2) is continued for 15 minutes to 180 minutes.
[8] The method according to any one of the above [5] to [7], wherein the contact in substep (A) is continued for 5 minutes to 30 minutes.
[9] The method according to any one of the above [1] to [8], wherein the cardiomyocyte population has a cardiomyocyte purity of 50% to 90%.
[10] A method for increasing the purity of cardiomyocytes in a cell population obtained by induced differentiation of pluripotent stem cells into cardiomyocytes, the method comprising
step 1: bringing the cell population into contact with a laminin selected from the group consisting of laminin α2β1γ1, laminin α2β2γ1, laminin α1β1γ1 and laminin α1β2γ1, or a fragment thereof having integrin binding activity, and
step 2: retrieving cells adherent to the laminin or the laminin fragment.
[11] The method according to the above [10], wherein the laminin fragment having integrin binding activity is a laminin E8 fragment.

Advantageous Effects of Invention

According to the present invention, a clinically applicable, safe and less damaged cardiomyocyte population can be prepared through a brief and simple procedure from a cell population obtained by induced differentiation of pluripotent stem cells into cardiomyocytes. In addition, according to the present invention, the purity of cardiomyocytes in a cell population obtained by induced differentiation or pluripotent stem cells into cardiomyocytes can be increased through a brief and simple procedure.

DESCRIPTION OF EMBODIMENTS

Method for Preparing Cardiomyocyte Population

Figure 1:
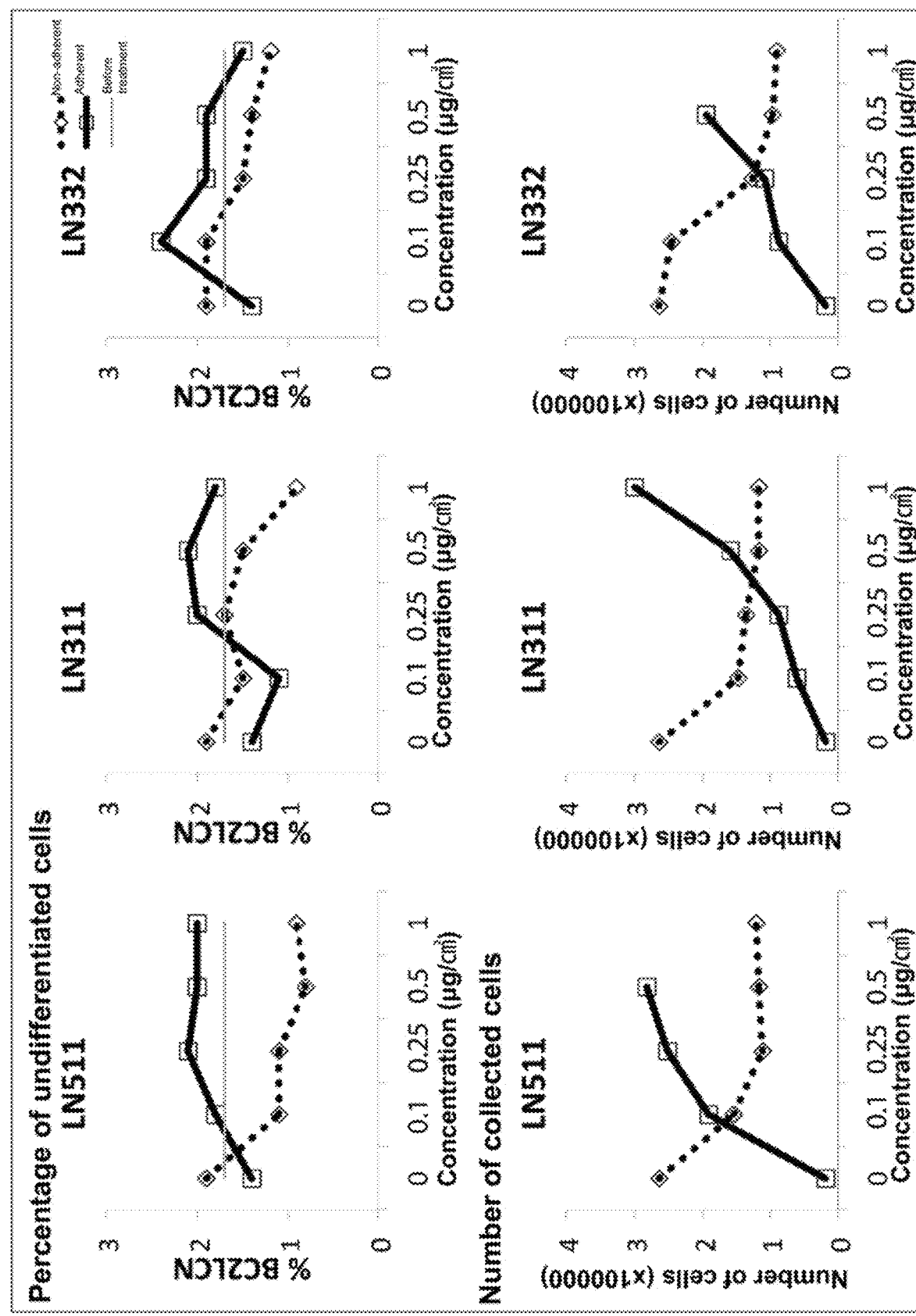
FIG. 1 shows the results of the examination of the effect of human laminin E8 fragments (511E8, 311E8 and 332E8) on the elimination of undifferentiated cells from a cell population obtained by induced differentiation of human iPS cells into cardiomyocytes.

The present invention provides a method for preparing a cardiomyocyte population (hereinafter referred to as "the preparation method of the present invention"). The preparation method of the present invention comprises at least the following steps (1) (2), and (3):
(1) inducing pluripotent stem cells to differentiate into cardiomyocytes,
(2) bringing a cell population obtained by the induced differentiation into contact with a laminin selected from the group consisting of laminin α2β1γ1, laminin α2β2γ1, laminin α1β1γ1 and laminin α1β2γ1, or a fragment thereof having integrin binding activity, and
(3) retrieving cells adherent to the laminin or the laminin fragment.
Preferably, the preparation method of the present invention further comprises a step of eliminating undifferentiated cells from a cell population obtained by induced differentiation of pluripotent stem cells into cardiomyocytes. Preferably, the step: of eliminating undifferentiated cells is performed between steps (1) and (2). A pluripotent stem cell-derived cardiomyocyte population having a smaller number of residual undifferentiated cells is considered much safer for transplantation.

The preparation method of the present invention may further comprise, after step (3), step (4) of culturing the cells retrieved in step (3).

In the step of eliminating undifferentiated cells, known methods for eliminating undifferentiated cells can preferably be used. The known methods for eliminating undifferentiated cells include the method described in WO 2012/056997, the method described in WO 2012/147992, the method described in WO 2012/133674, the method described in WO 2012/012803 (JP-W 2013-535194), the method described in WO 2012/078153 (JP-W 2014-501518), the method described in JP-A 2013-143968 and Cell Stem Cell Vol. 12 Jan. 2013, Page 127-137, and the method described in PNAS 2013 Aug. 27; 110(35); E3281-90.

In the preparation method, of the present invention, the method used in the step of eliminating undifferentiated cells preferably comprises the following substeps (A) and (B):
(A) bringing the cell population obtained by the induced differentiation into contact with a laminin selected from the group consisting of laminin α6β1γ1, laminin α5β2γ1, laminin α3β1γ1, laminin α3β2γ1 and laminin α3β3γ2, or a fragment thereof having integrin binding activity, and
(B) retrieving cells not adherent to the laminin or the laminin fragment.

The "cardiomyocyte population" obtained by the preparation method of the present invention means a cardiomyocyte-containing cell population obtained by induced differentiation of pluripotent stem cells. The "cardiomyocyte population" contains both mature cardiomyocytes and cardiac progenitor cells. The "cardiomyocyte population" may contain cells other than cardiomyocytes. Examples of the cells other than cardiomyocytes include cells of various stages in the differentiation process of pluripotent stem cells towards cardiomyocytes. In addition, vascular endothelial cells and vascular smooth muscle nails derived, by differentiation of pluripotent stem cells, and other cells may also be contained in the "cardiomyocyte population". The obtained cardiomyocyte population can preferably be used as a cardiomyocyte population for transplantation therapy in the clinical setting. For example, it can be used for preparation of cardiomyocyte sheets for transplantation and for direct injection into the heart via a catheter or a needle. In addition, the obtained cardiomyocyte population is very useful also as cells for research, such as new drug screening and embryological studies.

Examples of the pluripotent stem cells used in the preparation method of the present invention include ES cells (embryonic stem cells), iPS cells (induced pluripotent stem cells), mGS cells (multipotent germ stem cells) and hybridomas of ES cells and somatic cells. Preferred are ES cells and iPS cells, and more preferred are iPS cells. The pluripotent stem cells are preferably stem cells of mammals. The mammals are not particularly limited, and the examples include humans, mice, rats, cattle and pigs. Particularly preferred, are humans. The use of human pluripotent stem cells in the preparation method of the present invention enables the preparation of a cardiomyocyte population safe for humans.

Laminin is a heterotrimeric molecule consisting of three subunits termed α, β and γ chains. Five kinds of α chains (α1 to α5), three kinds of β chains (β1 to (β3) and three kinds of γ chains (γ1 to γ3) are known, and various combinations of these chains result in at least 12 kinds of laminin isoforms. The laminin used in step (2) of the preparation method of the present invention is preferably a laminin having binding specificity to integrins expressed on the surface of cardiomyocytes.

Laminin-binding integrins include integrin α3β1, integrin α6β1, integrin α6β4 and integrin α7β1 (Hynes et al., Cell Vol. 110, 673-687, 2002). These integrins have respective localized expression patterns in the living body, and integrin α7β1 is known to be selectively expressed in muscle tissues. Integrin α7β1 has two isoforms, namely, α7X1β1 and α7X2β1, which result from alternative splicing of the α7 chain, and cardiomyocytes and skeletal muscle cells are reported to dominantly express α7X2β1 (Israeli-Rosenberg et al., Circ Res. 2014; 114: 572-586). Among the laminin isoforms, laminin α2β1γ1, laminin α2β2γ1, laminin α1β1γ1 and laminin α1β2γ1 reportedly have high binding specificity to integrin α7X2β1 (Taniguchi et al., The Journal of Biological Chemistry, 7820-7831, 2009). Therefore, the laminin used in step (2) is preferably laminin α2β1γ1, laminin α2β2γ1, laminin α1β1γ1 or laminin α1β2γ1 due no the high binding specificity to integrin α7X2β1. Hereinafter, laminin α2β1γ1, laminin α2β2γ1, laminin α1β1γ1 and laminin α1β2γ1 are referred to as laminin 211, laminin 221, laminin 111 and laminin 121, respectively.

The laminin used in sub step (A) of the step of eliminating undifferentiated cells from a cell, population obtained by the induced differentiation in the preparation method of the present invention is preferably a laminin having binding specificity to integrins expressed on the surface of undifferentiated pluripotent stem cells. Pluripotent stem cells, in particular human pluripotent stem cells are known to more highly express α6β1 integrin than other integrins (Miyazaki T et al., Biochem. Biophys, Res. Commun., 375; 27-32, 2008). Among the laminin isoforms, laminin α5β1γ1, laminin α5β2γ1 and laminin α3β3γ2 reportedly have high binding specificity to integrin α6β1 (Nishiuchi et al., Matrix Biol., 25; 189-197, 2006). Therefore, the laminin used in substep (A) is preferably laminin α5β1γ1, laminin α5β2γ1 or laminin α3β3γ2 due to the high binding specificity to integrin α6β1. In addition, the present inventors have confirmed that laminin α3β1γ1 and laminin α3β2γ1, each of which has the α3 chain as with laminin α3β3γ2, also have high binding specificity to integrin α6β1. Therefore, these two laminin isoforms can also preferably be used in substep (A). Hereinafter, laminin α5β1γ1, laminin α5β2γ1, laminin α3β3γ2, laminin α3β1γ1 and laminin α3β2γ1 are referred to as laminin 511, laminin 521, laminin 332, laminin 311 and laminin 321, respectively.

The laminin used in the preparation method of the present invention may be a full-length laminin or a laminin fragment having integrin binding activity. That is, the laminin may be a full-length laminin consisting of a full-length α chain, a full-length β chain and a full-length γ chain, or a laminin fragment consisting of α, β and γ chains of which one or more are fragments shorter than the corresponding full-length chains. The laminin fragment is preferably a heterotrimeric laminin fragment. The integrin binding activity of the laminin fragment can be confirmed by, for example, a solid-phase binding assay using the integrin of interest. The heterotrimer formation of the laminin fragment Can be confirmed from, for example, the number of bands detected by SDS-PAGE.

A preferable example of the laminin fragment having integrin binding activity is a laminin, E8 fragment (hereinafter referred to as "laminin E8"). The laminin E8 is a heterotrimeric fragment obtained by elastase digestion of mouse laminin 111 and was identified as a fragment having a strong cell-adhesive activity (Edgar D et al., J. Cell Biol., 105: 589-598, 1987). Elastase digestion of laminins other than mouse laminin 111 could presumably produce fragments corresponding to the mouse laminin 111E8, but there is no report on isolation or identification of such laminin E8 fragments. Therefore, the laminin E8 used in the present invention does not have to be an elastase-digested product of laminins, and may be any laminin fragment having a cell-adhesive activity, structure and molecular weight equivalent to those of the mouse laminin 111E8.

The origin of the laminin or the laminin fragment is not particularly limited, and laminins or laminin fragments of various organisms can be used. Preferred are laminins or laminin fragments of mammals, including font not limited to humans, mice, rats, cattle and pigs. Particularly preferred is a human laminin fragment. For the preparation of a cardiomyocyte population safe for humans, it is recommended that no xenogeneic components are used in the preparation process, and therefore, a human laminin fragment is preferably used.

The laminin may be a native laminin or a modified laminin that has modification of one or more amino acid residues but retains biological activities of the native laminin. The method for producing the laminin is not particularly limited. For example, the laminin can be obtained by purification from cells expressing large amounts of the laminin. Alternatively, the laminin can be produced as a recombinant protein. The method for producing the laminin fragment is not particularly limited, either. For example, the laminin fragment can be obtained by digestion of a full-length laminin with a protease such as elastase, followed by isolation and purification of the fragment of interest. Alternatively, the laminin fragment can be produced as a recombinant protein. In terms of production quantity, quality uniformity, production cost, etc., it is preferred that the laminin and the laminin fragment are produced recombinant protein.

The recombinant laminin and the recombinant laminin fragment can be produced by appropriate known recombinant techniques, for example, by preparing DNAs encoding full-length or partial-length laminin α, β and γ chains, inserting the DNAs into separate expression vectors, cointroducing the three resulting expression vectors into appropriate host cells, and purifying the expressed trimeric protein by a known method. Examples of the method, for producing the recombinant laminin (full-length laminin) include, but are not limited to, the method of Ido et al. (Hiroyuki Ido et al., The Journal of Biological Chemistry, 279, 10946-10954, 2004). Examples of the method for producing of the recombinant laminin fragment (laminin E8) include, but are not limited to, the method of Ido et al. (Hiroyuki Ido et al., The Journal of Biological Chemistry, 282, 11144-11154, 2007).

Information regarding the nucleotide sequences of the genes encoding α, β and γ chains which constitute laminins of major mammals and the amino acid sequences of these chains can be obtained from known databases (e.g., GenBank). The accession numbers of the constituent chains of laminins of major mammals including humans are shown in Table 1. Information regarding the nucleotide and amino acid sequences of the constituent chains of laminins of other organisms can also be obtained from known databases (e.g., GenBank).

TABLE 1

|  | Amino acid sequence | Nucleotide sequence |
| --- | --- | --- |
| Human laminin α1 chain | NP_005550 | NM_005559 |
| Human laminin α2 chain | NP_000417 | NM_000426 |
| Human laminin α3 chain | NP_000218 | NM_000227 |
| Human laminin α4 chain | NP_002281 | NM_002290 |
| Human laminin α5 chain | NP_005551 | NM_005560 |
| Human laminin β1 chain | NP_002282 | NM_002291 |
| Human laminin β2 chain | NP_002283 | NM_002292 |
| Human laminin β3 chain | NP_000219 | NM_000228 |
| Human laminin γ1 chain | NP_002284 | NM_002293 |
| Human laminin γ2 chain | NP_005553 | NM_005562 |
| Human laminin γ3 chain | NP_006050 | NM_006059 |
| Mouse laminin α5 chain | NP_001074640 | NM_001081171 |
| Mouse laminin β1 chain | NP_032508 | NM_008482 |
| Mouse laminin γ1 chain | NP_034813 | NM_010683 |
| Rat laminin α5 chain | NP_001178538 | NM_001191609 |
| Rat laminin β1 chain | NP_001100191 | NM_001106721 |
| Rat laminin γ1 chain | NP_446418 | NM_053966 |

Laminin E8 is a trimeric fragment composed of a C-terminal fragment of the α chain lacking globular domains 4 and 5 (hereinafter referred to as "α chain E8"), a C-terminal fragment of the β chain (hereinafter referred to as "β chain E8"), and a C-terminal fragment of the γ chain (hereinafter referred to as "γ chain E8"), and the molecular weight of the trimer is about 150 to 170 kDa. The α chain E8 generally consists of about 770 amino acids, of which about 230 amino acids from the N-terminus are involved in the trimer formation. The β chain E8 generally consists of about 220 to 230 amino acids. The γ chain E8 generally consists of about 240 to 250 amino acids. The glutamic acid residue at the third position from the C-terminus of the γ chain E8 is essential for the integrin binding activity of laminin E8 (Hiroyuki Ido at al., The Journal of Biological Chemistry, 282, 11144-11154, 2007).

In step (1) of the present invention, known methods for induced differentiation of pluripotent stem cells into cardiomyocytes can preferably be used. Examples of the known methods include a method in which human pluripotent stem cells maintained on feeder cells are differentiated with activin A and BMP4 (bone morphogenetic protein 4) (Non Patent Literature 1 and 2), a method in which human pluripotent stem cells maintained on Matrigel are differentiated with Wnt3a, R-Spondin-1 and DKK1 (Non Patent Literature 3), a method in which human pluripotent stem cells maintained on feeder cells are differentiated on a large scale in a bioreactor (Non Patent Literature 3), and a method in which maintenance culture and subsequent induced, differentiation of human pluripotent stem cells are carried out using only chemically defined supplemental factors (WO 2014/078414). In particular, for the preparation of a cardiomyocyte population for human transplantation, for example, the above-mentioned method described in WO 2014/078414, a method in which human pluripotent stem cells maintained on human laminin 511E8 are differentiated into cardiomyocytes (JP-A 2011-078370) and the like are suitable.

In step (2) and substep (A) of the present invention, there is no particular limitation on the method for bringing a cardiomyocyte population obtained by the induced differentiation in step (1) into contact with a laminin or a fragment thereof. For example, the culture surface of a culture vessel, such as a culture dish, is coated with the laminin or a fragment thereof, and a cell suspension containing the cardiomyocyte population obtained by induced differentiation is added to the culture vessel and then incubated for a certain period of time. In another example, a carrier, such as beads, is coated with the laminin or a fragment thereof, added to a cell suspension containing the cardiomyocyte population obtained by induced differentiation, and then incubated for a certain period of time. In yet another example, the inner surface of a hallow fiber membrane used as a carrier is coated with the laminin or a fragment thereof, and a cell suspension containing the cardiomyocyte population obtained by induced differentiation is passed through the hollow fiber membrane.

In step (2) and substep (A), the coating concentration of the laminin or the laminin fragment is not particularly limited, and an appropriate coating concentration that attains the purpose of step (2) or substep (A) is selected. For example, the coating concentration is preferably selected from the range of about 0.1 to 2.0 µg/cm$^2$. In the case where laminin E8 is used in the preparation method of the present invention, the coating concentration of the laminin E8 in step (2) and substep (A) is particularly not limited, but is preferably about 0.1 to 2.0 µg/cm$^2$, more preferably about 0.25 to 1.0 µg/cm$^2$, still more preferably about 0.5 to 1.0 µg/cm$^2$.

In step (2) and substep (A), there is no particular limitation on the period for which the cells are in contact with the laminin or the laminin fragment (period of laminin treatment), and an appropriate period that attains the purpose of step (2) or substep (A) is selected according to the coating concentration, used. In the case where laminin E8 is used in the preparation method of the present invention, the period of the contact of the cells with the laminin E8 in step (2) is particularly not limited, but is preferably about 15 to 180 minutes, more preferably about 15 to 120 minutes, still more preferably about 15 to 60 minutes, yet still more preferably about 25 to 60 minutes. The period of the contact of the cells with the laminin E8 in substep (A) is also not particularly limited, but is preferably about 30 minutes or less, more preferably about 5 to 30 minutes, still more preferably about 5 to 15 minutes.

In step (3) of the present invention, there is no particular limitation on the method for retrieving cells adherent to the laminin or the laminin fragment, and an appropriate known method for detaching adherent cells can be selected. For example, after removing non-adherent cells, an EDTA solution is added onto a surface coated with the laminin or the laminin fragment, or a carrier coated with the laminin or the laminin fragment is added to an EDTA solution. The adherent cells are detached by pipetting or the like and then collected. Alternatively, a trypsin solution can be used for the detachment of the cells instead of the EDTA solution. In the case where step (3) is followed by step (4) of culturing the retrieved cells, step (3) may consist of only removing non-adherent cells.

In substep (B) of the present invention, there is no particular limitation on the method for retrieving cells not adherent to the laminin or the laminin fragment. For example, in the case where a culture vessel coated with the laminin or the laminin fragment is used, for example, the medium is collected from the culture vessel, the coated surface is washed a few times with PBS or the like, and the collected medium and wash solution are subjected to centrifugation or the like to collect the cells contained therein. In the case where a carrier coated with the laminin or the laminin fragment is added to a cell suspension, for example, the carrier is separated from the cell suspension, and the cell suspension free from the carrier is subjected to centrifugation or the like to collect the cells remaining therein. In the case where a hollow fiber membrane coated with the laminin or the laminin fragment is used, for example, a cell suspension passed, through the hollow fiber membrane is collected, and subjected to centrifugation or the like to collect the non-adherent cells.

In the preparation method of the present invention, in the case where step (3) is followed, by step (4) of culturing the cells retrieved in step (3), the culture method is not particularly limited, and can be selected from known cell culture methods as appropriate. Preferred is a culture method suitable for cardiomyocytes. For example, the cells can be cultured in the same culture vessel coated with a laminin or a fragment thereof as used in step (2). In a possible embodiment of step (3), the non-adherent cells after the completion of the laminin treatment are removed, a fresh medium is added to the cells adherent on the plate, and the cells kept on the plate are subjected to culture in step (4). The period of the culture is not particularly limited, and an appropriate period that is acceptable for the maintenance of a cardiomyocyte population with the desired cardiomyocyte purity is selected.

The purity of cardiomyocytes (the percentage of cardiomyocytes) in the cardiomyocyte population obtained by the preparation method of the present invention needs to be at least 10% or more, and is preferably 30% or more. More preferred is 50% to 90%, and still more preferred is 60% to 80%. The purity of cardiomyocytes (the percentage of cardiomyocytes) in the cardiomyocyte population can be determined as, for example, the percentage of cardiac troponin T-positive cells in the cardiomyocyte population as measured by flow cytometry or the like.

There is no particular limitation on the percentage or undifferentiated cells in the cardiomyocyte population obtained by the preparer ion method of the present invention. In the preparation method of the present invention, it is preferable that the step of eliminating undifferentiated cells is performed between steps (1) and (2). In this case, the number of undifferentiated cells in the cardiomyocyte population can be reduced as compared with in the case where the step of eliminating undifferentiated cells is not performed. In particular, in the case where substeps (A) and (B) are employed in the step of eliminating undifferentiated cells, undifferentiated cells can be eliminated without damage to the cardiomyocyte population. The percentage of undifferentiated cells in the cardiomyocyte population can be determined as, for example, the percentage of BC2LCN-positive cells in the cardiomyocyte population as measured by flow cytometry or the like.

The preparation method of the present invention is characterized by bringing cell population obtained by induced differentiation of pluripotent stem cells into cardiomyocytes into contact with a laminin or a laminin fragment and subsequently retrieving cells adherent to the laminin or the laminin fragment. The preparation method of the present invention is advantageous over other preparation methods in terms of the following. Firstly, the procedure is simple and very brief. In conventional preparation methods, the selection of cardiomyocytes utilizes the difference in the metabolic pathway between cardiomyocytes and other cells, in particular, between cardiomyocytes and cells remaining undifferentiated. For this reason, the selection procedure requires a long period of time (at least a few days). Such a selection procedure is greatly stressful to cells and inevitably compromises the viability of the selected cells. In the preparation method of the present invention, however, the selection procedure requires only a few minutes to a few hours and is considerably less stressful to cells. Secondly, since the selection of the cells of interest utilizes integrin-mediated cell adhesion to substrates, the viability of the cells is expected to be improved rather than compromised. In fact, integrin-dependent cell adhesion to laminins is known to prevent cell apoptosis and maintain cell survival, and also known to activate intracellular signaling pathways that promote; cell growth (Gu J et al., The Journal of Biological Chemistry 277: 19922-19928, 2002). Therefore, the preparation method of the present invention is greatly advantageous in that a cardiomyocyte population obtained by induced differentiation of pluripotent stem cells can be selected in a short time while maintained in a highly viable state, unlike the conventional preparation methods. Moreover, it is easy to successively repeat the procedure of step (2) or a series of the procedures of steps (2) and (3) in the preparation method of the present invention. Such a successive repetition of the procedure can readily result in an increased cardiomyocyte purity in the cardiomyocyte population. As described above, the cardiomyocyte population obtained by the preparation method of the present invention is very highly safe and also highly viable, and therefore, is very excellent for transplantation.

The laminins that can be used in step (2) of the preparation method of the present invention, namely laminin 211, laminin 221, laminin 111 and laminin α121, have binding specificity not only to cardiomyocytes but also to skeletal muscle cells. For this reason, in the case where step (1) is changed to the step of inducing pluripotent stem cells to differentiate into skeletal muscle cells, a method for preparing skeletal muscle cells can be provided.

Moreover, in the case where different types of laminins are used depending on the type of the cells of interest in step (2) of the preparation method of the present invention, various types of cells derived by differentiation of pluripotent stem cells can be selected in a cell adhesion dependent manner using substrates coated with appropriate laminins. Specifically, hepatic progenitor cells derived by differentiation of human pluripotent stem cells reportedly adhere to laminin 111 in an integrin α6β1 dependent manner (Takayama K. et al., Stem Cell Reports 1: 322-335, 2013). Also reported is transient expression of laminin 111 in regenerating livers (Kikkawa Y et al., Experimental Cell Research 305: 99-109, 2005). These findings indicate that hepatic progenitor cells derived by differentiation of human pluripotent stem cells can be selected and purified using substrates coated with laminin 111. That is, in the case where step (1) is changed to the step of inducing pluripotent stem cells to differentiate into hepatic progenitor cells and laminin 111 is used in step (2) in the preparation method of the present invention, a method for preparing hepatic progenitor can be provided.

Method for Increasing the Purity of Cardiomyocytes

The present invention provides a method for increasing the purity of cardiomyocytes in a cell population obtained by induced differentiation of pluripotent stem cells into cardiomyocytes. The method of the present invention for increasing the purity of cardiomyocytes comprises at least the following steps 1 and 2:

step 1: bringing the cell population into contact with a laminin selected from the group consisting of laminin α2β1γ1, laminin α2β2γ1, laminin α1β1γ1 and laminin α1β2γ1, or a fragment thereof having integrin binding activity, and step 2: retrieving cells adherent to the laminin or the laminin fragment.

The details of steps 1 and 2 are the same as those of steps (2) and (3) in the above-described preparation method of the present invention. The method of the present invention for increasing the purity of cardiomyocytes can be performed in the same manner as in the above-described preparation method of the present invention.

EXAMPLES

Hereinafter, the present invention will be illustrated in detail by examples, but the present invention is not limited thereto.

Experimental Materials and Methods (1) Human Laminin E8s

Five hinds of human laminin E8s were used in the experiments shown below and were human laminin 511E8, human laminin 332E8, human laminin 311E8 human laminin 221E8 and human laminin 211E8. Hereinafter in the examples, human laminin 511E8, human laminin 332E8, human laminin 311E8, human laminin 221E8 and human, laminin 211E8 are abbreviated as 511E8, 332E8, 311E8, 221E8 and 211E8, respectively.

The 511E8 used was a purchased product, iMatrix-511 (trade name, Nippi Inc.). The laminin E8s other than 511E8 were produced according to the methods described in Ido et al, (Hiroyuki Ido et al., The Journal of Biological Chemistry, 282, 11144-11154, 2007) and Taniguchi et al. (Yukimasa Taniguchi et al., The Journal of Biological Chemistry, 7820-7831, 2009). The specific procedure was as follows. An expression vector for the human α3 chain E8 fragment (containing the 6×His tag in the N-terminal region), an expression vector for the human α2 chain E8 fragment (containing the 6×His tag in the N-terminal region), an expression vector for the human β3 chain E8 fragment (containing the HA tag in the N-terminal region), an expression vector for the human β2 chain E8 fragment (containing the HA tag in the N-terminal region), an expression vector for the human β1 chain E8 fragment (containing the HA tag in the N-terminal region), an expression vector for the human γ2 chain E8 fragment (containing the FLAG tag in the N-terminal region) and an expression vector for the human γ1 chain E8 fragment (containing the FLAG tag in the N-terminal region) were prepared. Appropriate combinations of the prepared expression vectors for the α, β and γ chains were separately transfected into human embryonic kidney 293 cells. After 72 hours of culture, the culture media were collected and subjected to affinity chromatography using Ni-NTA agarose and AHTI-FLAG M2 Affinity Gel for the purification of the laminin E8s of interest.

(2) Coating of Culture Plates with Laminin E8s

The culture plates used were 6-well or 12-well multiwell plates (BD Falcon). The laminin E8s of interest were diluted to desired concentrations in PBS, and added in a volume of 1 mL (6-well) or 0.4 mL (12-well) per well. After 2 hours or more of incubation at 37° C., the laminin solution was removed and the coated surface was washed twice with PBS. The coating of the culture plates was performed just before use. Six-well multiwell plates were used in Examples 1 to 4 and 9, and 12-well multiwell plates were used in Examples 5 to 8.

(3) Induced Differentiation of Human IPS Cells into Cardiomyocytes

The human iPS cell line 253G1 was purchased from RIKEN. Myocardial differentiation was performed in a reactor according to the method described in Matsuura et al. (Matsuura et al., Biochem Biophys Res Commun, 2012 Aug. 24; 425(2): 321-7, doi: 10.1016/j.bbrc.2012.07.089. Epub 2012 Jul. 25). The specific procedure was as follows. Undifferentiated 253G1 cells were cultured on mitomycin-C-treated MSFs in Primate ES medium (ReproCELL Inc.) supplemented with 5 ng/mL bFGF, which was used as a medium for maintenance of undifferentiated state. The undifferentiated 253G1 cells on ten 10-cm culture dishes were collected with the addition of a cell detachment solution (ReproCELL Inc.) and suspended in 100 mL of mTeSR medium (STEMCELL Technologies) supplemented with 10 µM Y27632 (ROCK inhibitor). The cell suspension was transferred to a vessel in a bioreactor system (ABLE Corporation) and agitation culture was started. One day later, Y27632 was eliminated from the medium. One day after the onset of the agitation culture, the medium was replaced with StemPro-34 (Life Technologies). Three days after the onset of the agitation culture, 0.5 ng/mL BMP4 was added to the medium. Four days after the onset of the agitation culture, 10 ng/mL BMP4, 5 ng/mL bFGF and 3 ng/mL activin A were added to the medium. Seven days after the onset of the agitation culture, 4 µM IWR-1 was added to the medium. Nine days after the onset of the agitation culture, 5 ng/mL VSGF and 10 ng/mL bFGF were added to the medium. The agitation culture was further continued, and 16 to 18 days after the onset of the agitation culture, the cells were collected.

(4) Preparation of Cell Suspension after Induced Differentiation

After the induced differentiation of the 253G1 cells into cardiomyocytes, clumps of the cells were dissociated with the addition of a 0.05% trypsin-EDTA solution (Life Technologies). The cells were filtered through a 70-µm mesh filter, and a cell suspension was prepared. The cell suspension was centrifuged at 1500 rpm for 5 minutes. The pellet was suspended in PBS and the suspension was centrifuged at 1500 rpm for 5 minutes again. The pellet was suspended at 200,000 cells/mL in medium (DMEM supplemented with 1% bovine serum albumin).

(5) Laminin Treatment

The cell suspension was added in a volume of 3 ml (600,000 cells) to each well of the 6-well multiwell plate coated with the laminin E8s of interest. Alternatively, the cell suspension was added in a volume of 1.2 mL (240,000 cells) to each well of the 12-well multiwell plate coated with the Laminin E6s of interest. After a certain period of treatment (contact period), non-adherent cells and adherent cells were separately collected. The specific procedure was as follows. The culture supernatant was collected, the culture surface was washed with PBS, and the wash solution was collected. The culture surface was washed again with PBS and the wash solution was collected. The cells contained in the culture supernatant and the wash solutions collected twice were called non-adherent cells. Onto the culture surface washed twice with PBS, an EDTA solution was added and the cells were detached by pipetting to collect the cells. The culture surface was washed with PBS and the wash solution was collected. The cells detached with EDTA and the cells contained in the collected wash solution were called adherent cells.

The non-adherent cells and the adherent cells were separately centrifuged (at 1500 rpm for 5 minutes), and the supernatants were removed. The pellets were stained with anti-cardiac troponin T (for detection of cardiomyocytes) or BC2LCN (for detection of undifferentiated cells) and analyzed by flow cytometry or immunostaining.

Example 1: Elimination of Undifferentiated Cells from Cell Suspension Using 511E8, 311E8 and 332E8

After the induced differentiation of the 253G1 cells into cardiomyocytes, the cells were treated with 511E8, 311E8 or 332E8 for 30 minutes. After that, non-adherent cells and adherent cells were separately collected. Each of the laminin E8s was used at 5-graded concentrations of 0, 1, 2.5, 5 and 10 µg/mL (0, 0.1, 0.25, 0.5 and 1 µg/cm$^2$). The percentages of BC2LCN-positive cells (the percentages of undifferentiated cells) in the collected non-adherent cells and in the collected adherent cells were evaluated by flow cytometry.

The results are shown in FIG. 1. The percentages of undifferentiated cells are shown in the upper row, and the numbers of the collected cells are shown in the lower row. In the figure, LN511 stands for 511E8, LN311 stands for 311E8, and LN332 stands for 332E8. The percentage of undifferentiated cells before the laminin treatment was 1.7%, but the percentage of undifferentiated cells in the non-adherent cells collected after the laminin E8 treatment decreased in a laminin E8 concentration dependent manner regardless of the type of the laminin E8. In particular, in the case of the treatment with 511E8, the reduction in the percentage of undifferentiated cells was observed even at low concentrations, and the percentage of undifferentiated cells at a coating concentration of 0.5 µg/cm$^2$ was as low as 0.8%. The number of the collected non-adherent cells was reduced by the treatment with any of the laminin E8s in a concentration dependent manner.

Example 2: Specificity of 511E8 to Undifferentiated Cells

After the induced differentiation of the 253G1 cells into cardiomyocytes, the cells were treated with 511E8 at a coating concentration of 0.5 µg/cm$^2$ or with 221E8 at a coating concentration of 1 µg/cm$^2$ for 30 minutes. After that, non-adherent cells and adherent cells were separately collected. The percentages of BC2LCN-positive cells (the percentages of undifferentiated cells) in the collected non-adherent cells and in the collected adherent cells were evaluated by flow cytometry.

Figure 2:
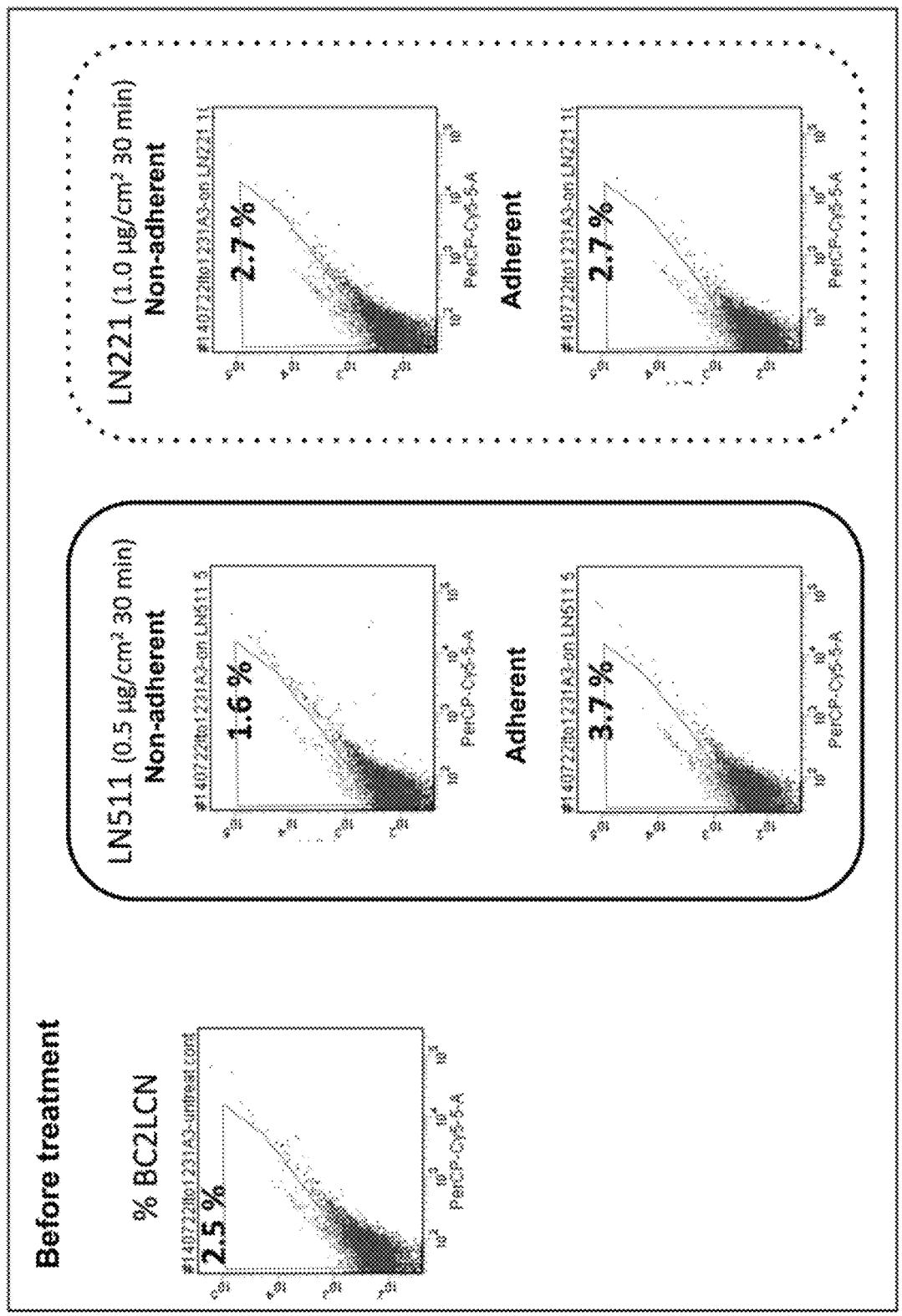
FIG. 2 shows the results of the comparison of the specificity to undifferentiated cells between the human laminin SUES fragment and the human laminin 221E8 fragment.

The results are shown in FIG. 2. In the figure, LN511 stands for 511E8 and LN221 stands for 221E8. The percentage of undifferentiated cells before the treatment was 2.5%, but the percentage of undifferentiated cells in the non-adherent cells collected after the treatment with 511E8 at 0.5 µg/cm$^2$ was 1.6%, which was lower than the level before the treatment. Meanwhile, the percentage of undifferentiated cells in the adherent cells was 3.7%, which was higher than the level, before the treatment. On the other hand, the percentages of undifferentiated cells in the non-adherent cells and in the adherent cells collected after the treatment with laminin 221 at 1 µg/cm$^2$ were each 2.7%.

Example 3: Isolation of Cardiomyocytes Using 221E8, 211E8 and 511E8 and Specificity of these Laminin E8s to Cardiomyocytes After the induced differentiation of the 253G1 cells into cardiomyocytes, the cells were treated with 221E8, 211E8 or 511E8 for 30 minutes. After that, non-adherent cells and adherent cells were separately collected. Each of the laminin E8s was used at 5-graded coating concentrations of 0, 0.25, 0.5, 1 and 2 µg/cm$^2$. The percentages of cardiac troponin T-positive cells (the percentage of cardiomyocytes) in the collected non-adherent cells and in the collected adherent cells were evaluated by flow cytometry.

Figure 3:
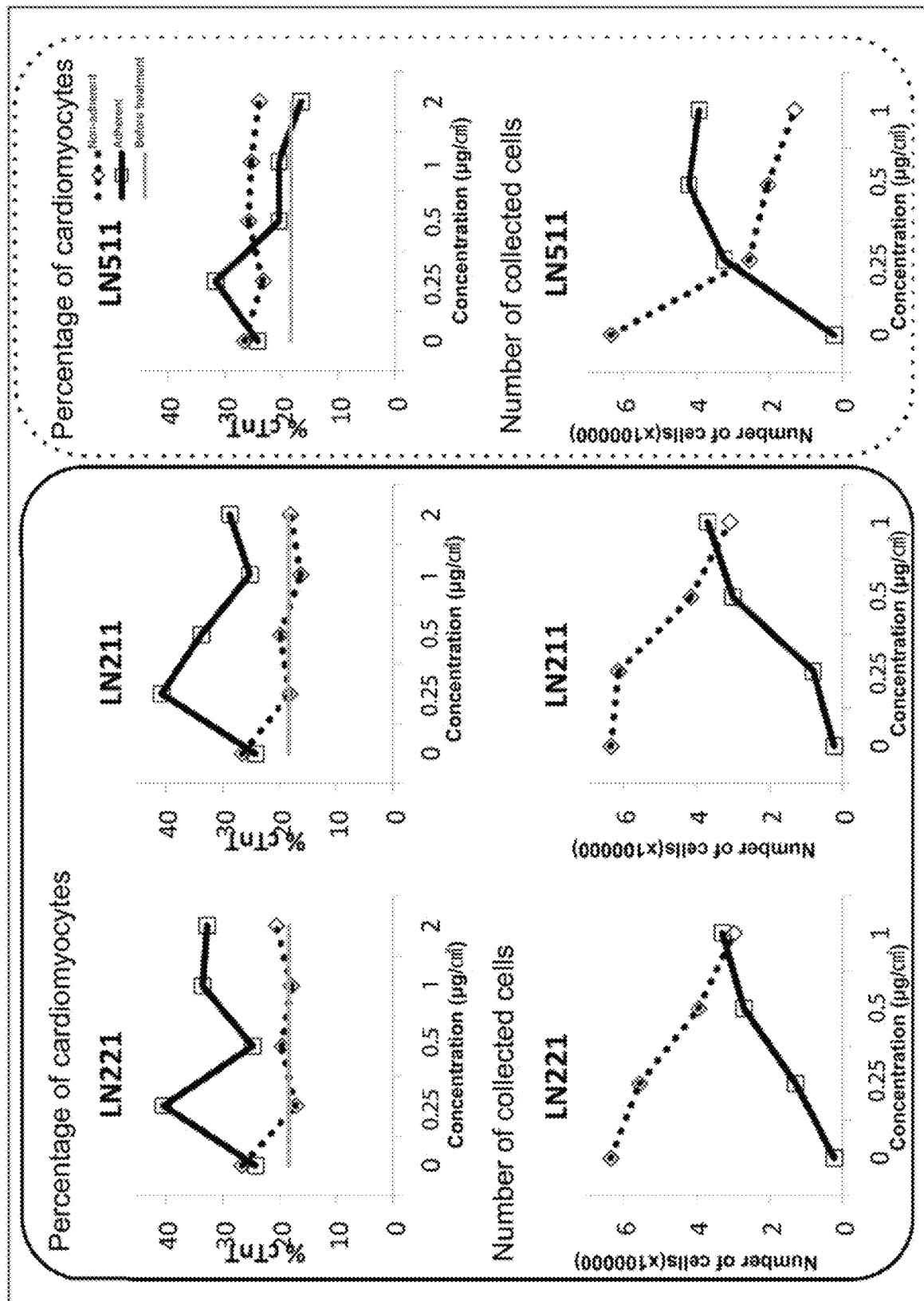
FIG. 3 shows the results of the examination of the effect of human laminin E8 fragments (221E8, 211E8 and 511E8) on increasing the percentage of cardiomyocytes in a cell population obtained by induced differentiation of human iPS cells into cardiomyocytes and also shows the results of the examination of the specificity of the human laminin E8 fragments to cardiomyocytes.

The results are shown in FIG. 3. The percentages of cardiac troponin T-positive cells (the percentage of cardiomyocytes) are shown in the upper row, and the numbers of the collected cells are shown in the lower row. In the figure LN221 stands for 221E8, LN211 stands for 211E8, and LN511 stands for 511E8. The percentage of cardiomyocytes before the laminin treatment was 18.5%. The percentage of cardiomyocytes in the non-adherent cells collected after the laminin E8 treatment was almost comparable to the level before the treatment regardless of the type of the laminin E8, but the percentage of cardiomyocytes in the adherent cells collected after the treatment with 221E8 was higher than the level before the treatment. On the other hand, there was no great difference in the percentages of cardiomyocytes between the adherent cells and the non-adherent cells collected after the treatment with 511E8. The number of the collected adherent cells was increased by the treatment with any of the laminin E8s in a concentration dependent manner.

Example 4: Time-Course Changes in Dumber of Adherent Cells and in Percentage of Cardiomyocytes Upon 221E8 Treatment After the induced differentiation of the 253G1 cells into cardiomyocytes, the cells were treated with 221E8 at a coating concentration of 1 μg/cm$^2$, and adherent cells were collected over time. The number of the collected cells and the percentage of cardiomyocytes (the percentage of cardiac troponin T-positive cells) in the collected cells were evaluated by flow cytometry.

Figure 4:
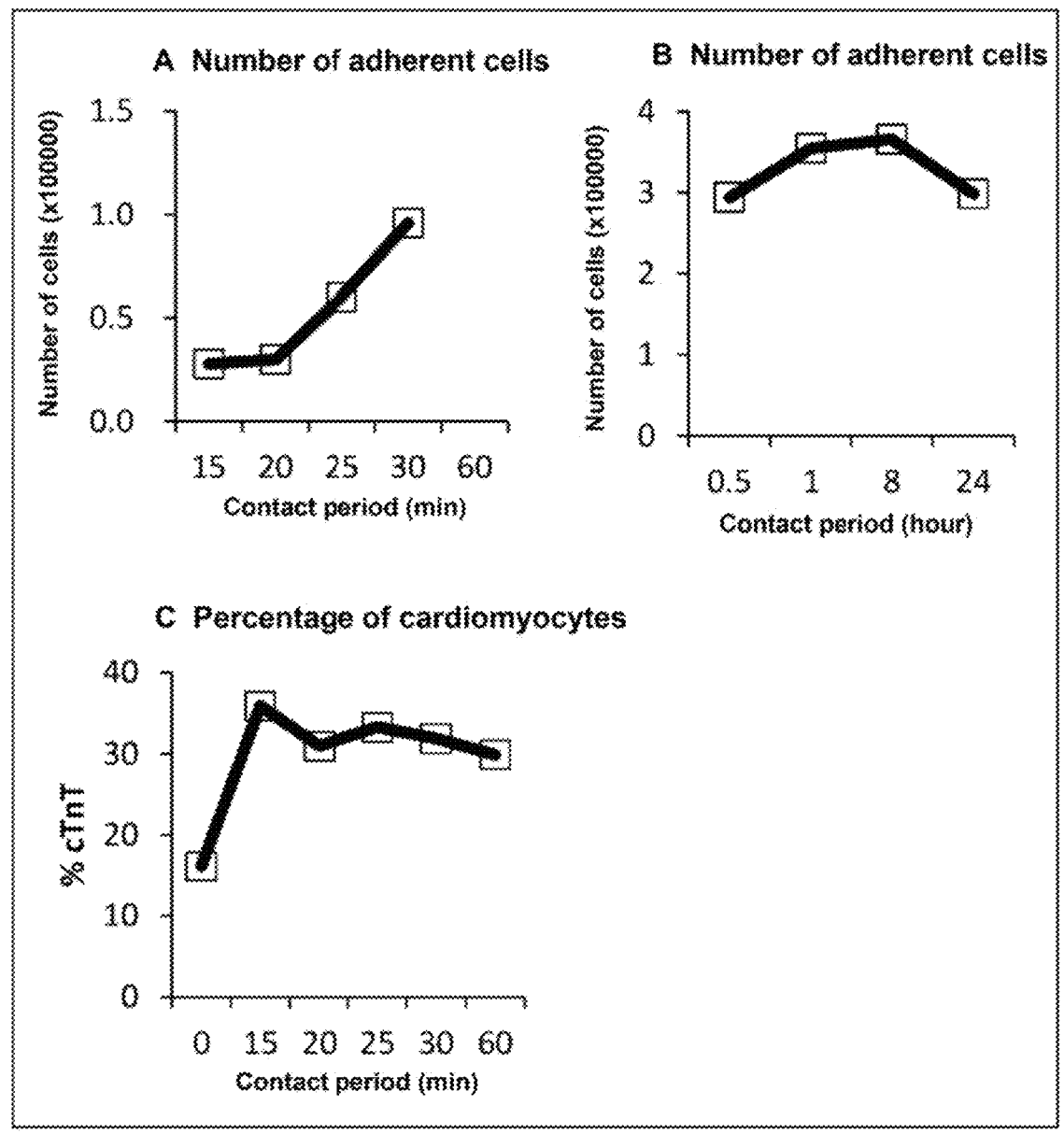
FIG. 4 shows the results of the examination of the percentage of cardiomyocytes in adherent cells collected over time after treatment with human laminin 221E8 fragment in a cell population obtained by induced differentiation of human iPS cells into cardiomyocytes.

The results are shown in FIGS. 4A, 4B and 4C. FIG. 4A shows the number of the adherent cells after 15, 20, 25 and 30 minutes of the treatment with 221E8, FIG. 4B shows the number of the adherent cells after 0.5, 1, 8 and 24 hours of the treatment with 221E8 (the results of an experiment independent from that in FIG. 4A), and FIG. 4C shows the percentage of cardiomyocytes in the adherent cells after 15, 28, 25, 30 and 60 minutes of the treatment with 221E8. The percentage of cardiomyocytes at a contact time point of 0 min is the percentage of cardiomyocytes before the treatment with 221E8. The number of the adherent cells increased over time from 15 to 30 minutes after the onset of the treatment with 221E8 (FIG. 4A). The number of the adherent cells continued to increase gradually from 1 to 8 hours after the onset of the treatment, and then tended to decrease until 24 hours after the onset of the treatment (FIG. 4B). The percentage of cardiomyocytes before the treatment with 221E8 was 16.1%. The percentage of cardiomyocytes increased to 35.9% after 15 minutes of the treatment with 221E8, and from then on, tended to decrease over time (FIG. 4C).

Example 5: Elimination of Undifferentiated Cells from Cell Suspension Using 511E8, 211E8 and 211E8

After the induced differentiation of the 253G1 cells into cardiomyocytes, the cells were treated with 511E8, 211E8 or 221E8 at a coating concentration of 1 μg/cm$^2$, and non-adherent cells were collected at 15, 30, 60 and 120 minutes from the onset of the treatment. The number of the collected non-adherent cells and the relative amount of undifferentiated cells (the relative amount of BC2LCN-positive cells) were evaluated by flow cytometry. The relative amount of undifferentiated cells was expressed as a ratio relative to the percentage of undifferentiated cells before the treatment, that is, as a value obtained by division of the percentage of BC2LCN-positive cells after the treatment by the percentage of BC2LCN-positive cells before the treatment.

Figure 5:
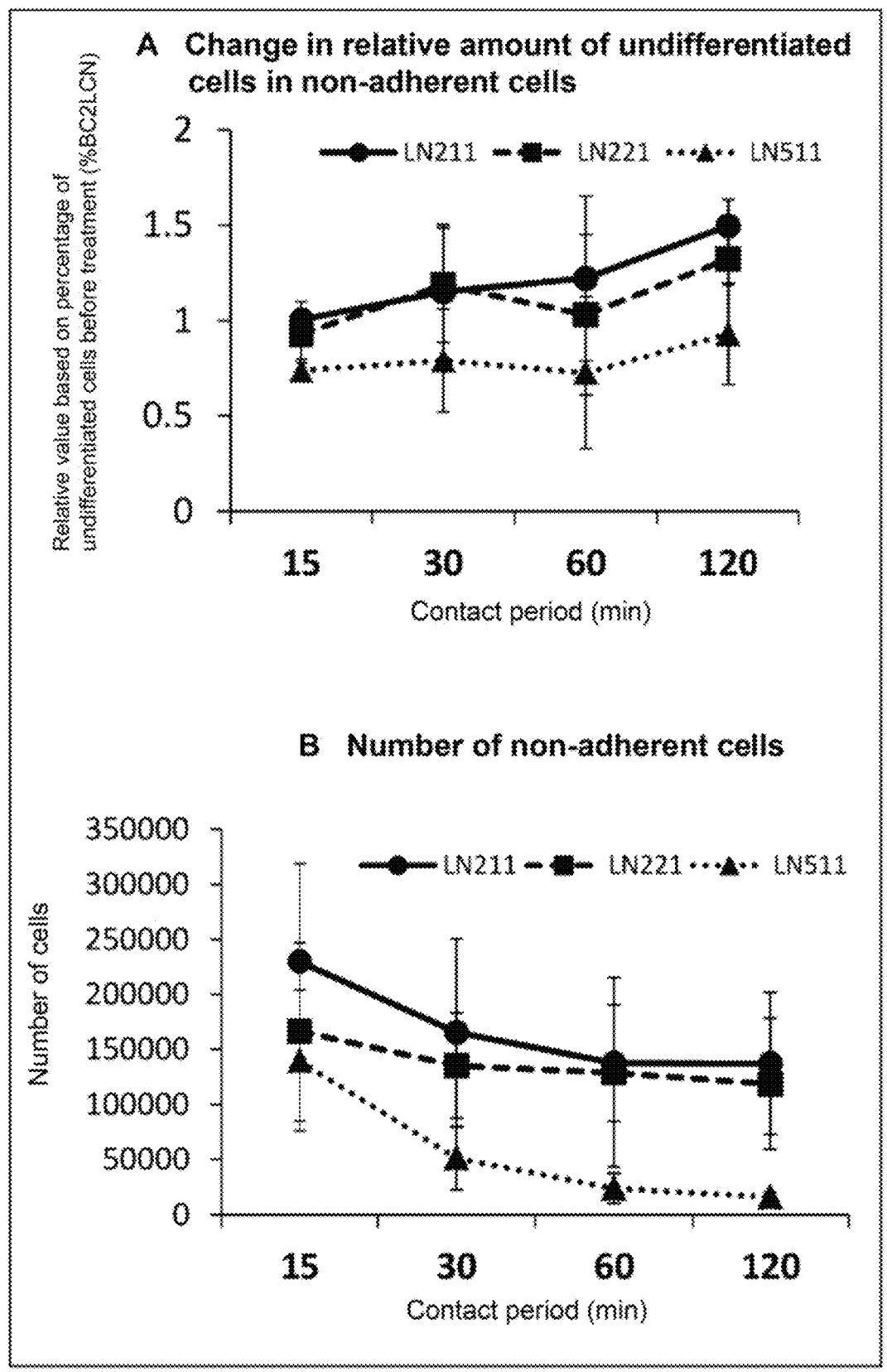
FIG. 5 shows the results of the examination of the effect of various periods of treatment (contact) with human laminin E8 fragments (511E8, 221E8 and 211E8) on the elimination of undifferentiated cells from a cell population obtained by induced differentiation of human iPS cells into cardiomyocytes.

The results are shown in FIGS. 5A and 5B. FIG. 5A shows the time-course changes in the relative amount of undifferentiated cells in the non-adherent cells, and FIG. 5B shows the number of the non-adherent cells at each collection time point. In the figures, LN511 stands for 511E8, LN221 stands for 221E8, and LN211 stands for 211E8. As shown in FIG. 5A, the relative amount of undifferentiated cells after the treatment with 211E8 or 221E8 was about 1 or more at each collection time point, but the relative amount of undifferentiated cells after the treatment with 511E8 was less than 1 at each collection time point. These results show that the treatment with 511E8 is effective for the elimination of undifferentiated cells from the cell suspension. As shown in FIG. 5B, the number of the collected non-adherent cells decreased in a contact period dependent manner regardless of the type of the laminin, but the number of the non-adherent cells after the contact with 511E8 remarkably decreased after 30 minutes or more of the contact. These results indicate that the period of the contact of the cells with the laminin E8 in substep (A) in the step of eliminating undifferentiated cells is preferably 30 minutes or less, more preferably 15 minutes or less in view of the time-course change in the relative amount of undifferentiated cells and the time-course change in the number of the non-adherent cells.

Example 6: Purification of Cardiomyocytes Using 511E8, 211E8 and 221E8: Examination of Treatment Period (1) Changes in Relative Amount of Cardiomyocytes and in Number of Adherent Cells with variation in Treatment Period (Contact Period)

After the induced differentiation of the 253G1 cells into cardiomyocytes, the cells were treated with 511E8, 211E8 or 221E8 at a coating concentration of 1 μg/cm$^2$, and adherent cells were collected at 15, 30, 60 and 120 minutes from the onset of the treatment. The number of the collected adherent cells and the relative amount of cardiomyocytes (the relative amount of cardiac troponin T-positive cells) were evaluated by flow cytometry. The relative amount of cardiomyocytes was expressed as a ratio relative to the percentage of cardiomyocytes before the treatment, that is, as a value obtained by division of the percentage of cardiac troponin T-positive cells after the treatment by the percentage of cardiac troponin T-positive cells before the treatment.

Figure 6:
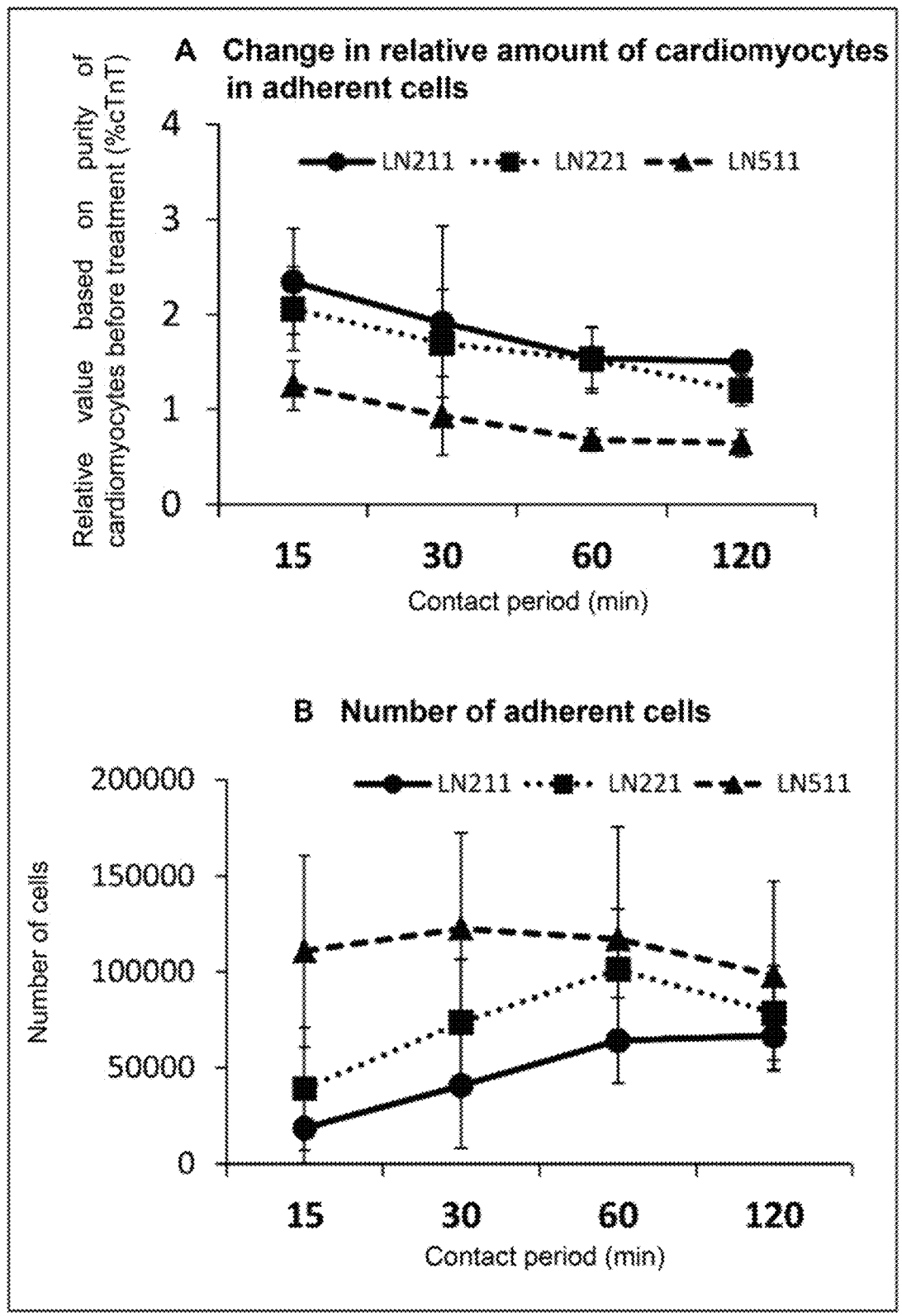
FIG. 6 shows the results of the examination of the effect of various periods of treatment (contact) with human laminin E8 fragments (511E8, 221E8 and 211E8) on the purification of cardiomyocytes in a cell population obtained by induced differentiation of human iPS cells into cardiomyocytes.

The results are shown in FIGS. 6A and 6B. FIG. 6A shows the time-course changes in the relative amount of cardiomyocytes in the adherent cells, and FIG. 6B shows the number of the adherent cells at each collection time point. In the figures, LN511 stands for 511E8, LN221 stands for 221E8, and LN211 stands for 211E8. As shown in FIG. 6A, the relative amount of cardiomyocytes after the treatment with 511E8 was about 1 at each collection time point, but the relative amount of cardiomyocytes after the treatment with 211E8 or 221E8 was more than 1 at each collection time point. These results show that the treatment with 211E8 or 221E8 and the subsequent collection of the adherent cells were effective for increasing the purity of cardiomyocytes. As shown in FIG. 6B, the number of the adherent cells collected after the treatment with 211E8 or 221E8 increased in a time dependent manner until 60 minutes after the onset of the treatment (contact). These results indicate that the period of the contact of the cells with the laminin E8 in step (2) in the preparation method of the present invention is preferably about 30 to 60 minutes.

Example 7: Purification of Cardiomyocytes Using 511E8, 211E8 and 221E8: Examination of Laminin E8 Coating Concentration After the induced differentiation of the 253G1 into cardiomyocytes, the cells were treated with 511E8, 211E8 or 221E8 at 4-graded coating concentrations of 0.25, 0.5, 1 and 2 μg/cm$^2$, and adherent cells were collected at 30 minutes from the onset of the treatment. The number of the collected adherent cells and the relative amount of cardiomyocytes (the relative amount of cardiac troponin T-positive cells) were evaluated by flow cytometry. The relative amount of cardiomyocytes was expressed as a ratio relative to the percentage of cardiomyocytes before the treatment, that is, as a value obtained by division of the percentage of cardiac troponin T-positive cells after the treatment by the percentage of cardiac troponin T-positive cells before the treatment.

Figure 7:
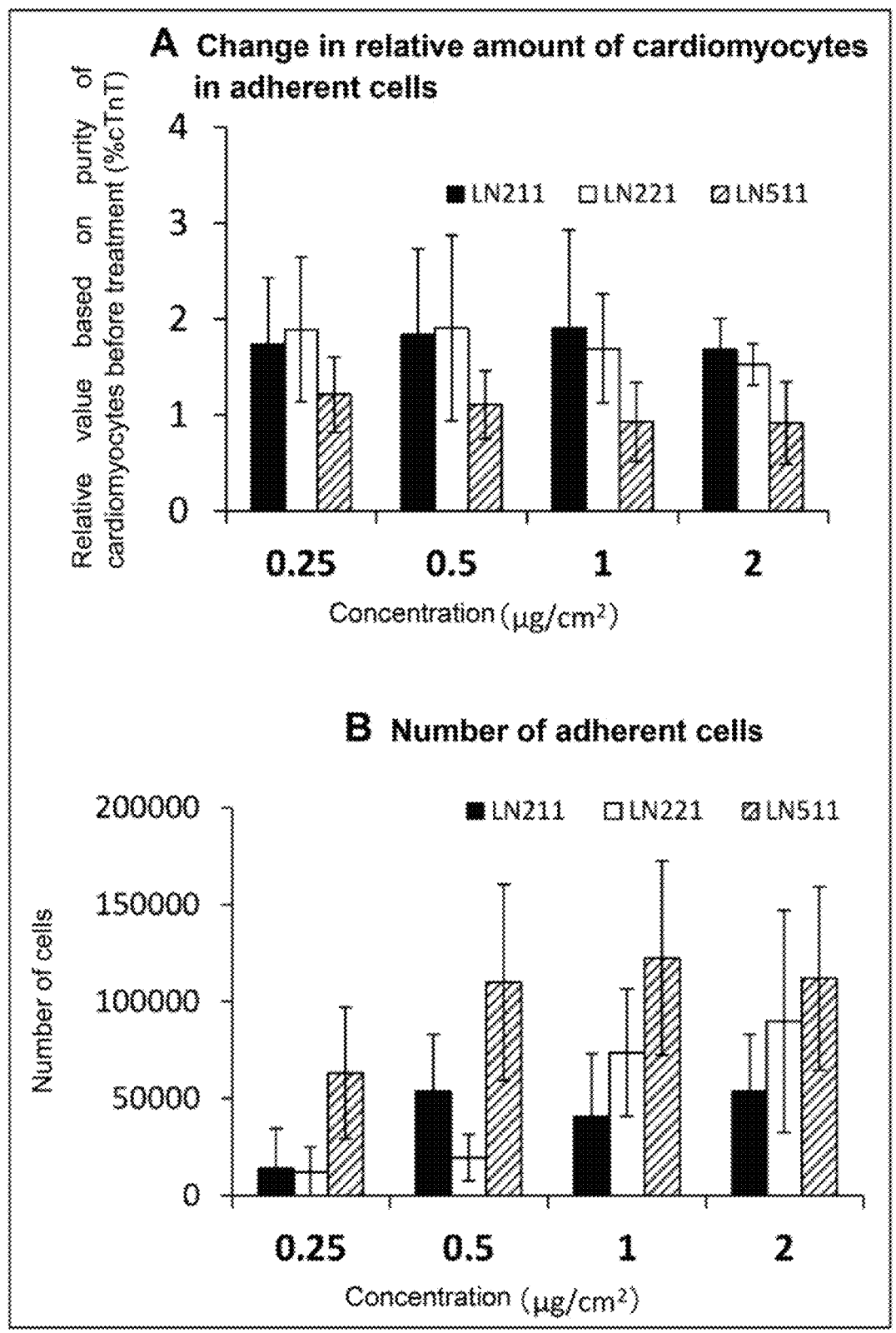
FIG. 7 shows the results of the examination of the effect of various coating concentrations of human laminin E8 fragments (511E8, 221E8 and 211E8) on the purification of cardiomyocytes in a cell population obtained by induced differentiation of human iPS cells into cardiomyocytes.

The results are shown in FIGS. 7A and 7B. FIG. 7A shows the relative amount of cardiomyocytes in the adherent cells at each coating concentration, and FIG. 7B shows the number of the adherent cells at each coating concentration. In the figures, LN511 stands for 511E8, LN221 stands for 221E8, and LN211 stands for 211E8, As shown in FIG. 7A, the relative amount of cardiomyocytes after the treatment with 511E8 was about 1 at each coating concentration, but the relative amount of cardiomyocytes after the treatment with 211E8 or 221E8 was more than 1 at each coating concentration. These results show that the treatment with 211E8 or 221E8 and the subsequent collection of the adherent cells were effective for increasing the purity of cardiomyocytes. As shown in FIG. 7B, the number of the adherent cells collected after the treatment with 211E8 increased in a coating concentration dependent manner within the range up to 0.5 μg/cm$^2$, and the number of the adherent cells collected after the treatment with 221E8 increased in a coating concentration dependent manner within the range up to 2 μg/cm$^2$. These results indicate that the coating concentration of the laminin E8 in step (2) in the preparation method of the present invention is preferably about 0.5 to 2 μg/cm$^2$.

Example 8: Confirmation of Effect of 221E8 on Enrichment of Cardiomyocytes

After the induced differentiation of the 253G1 cells into cardiomyocytes, the cells were treated with 511E8 or 221E8 at a coating concentration of 1 μg/cm$^2$ for 30 minutes. After that, adherent cells were collected and the percentage of cardiomyocytes (the percentage of cardiac troponin T-positive cells) in the collected adherent cells was measured by flow cytometry. In a separate experiment, after the 30-minute treatment, non-adherent cells were removed, adherent cells were cultured for 3 days on a plate coated with 1 μg/cm$^2$ 511E8 or 221E8, and immunostained for detection of cardiac troponin T-positive cells. The cells were also stained with DAPI for nuclear counterstaining.

Figure 8:
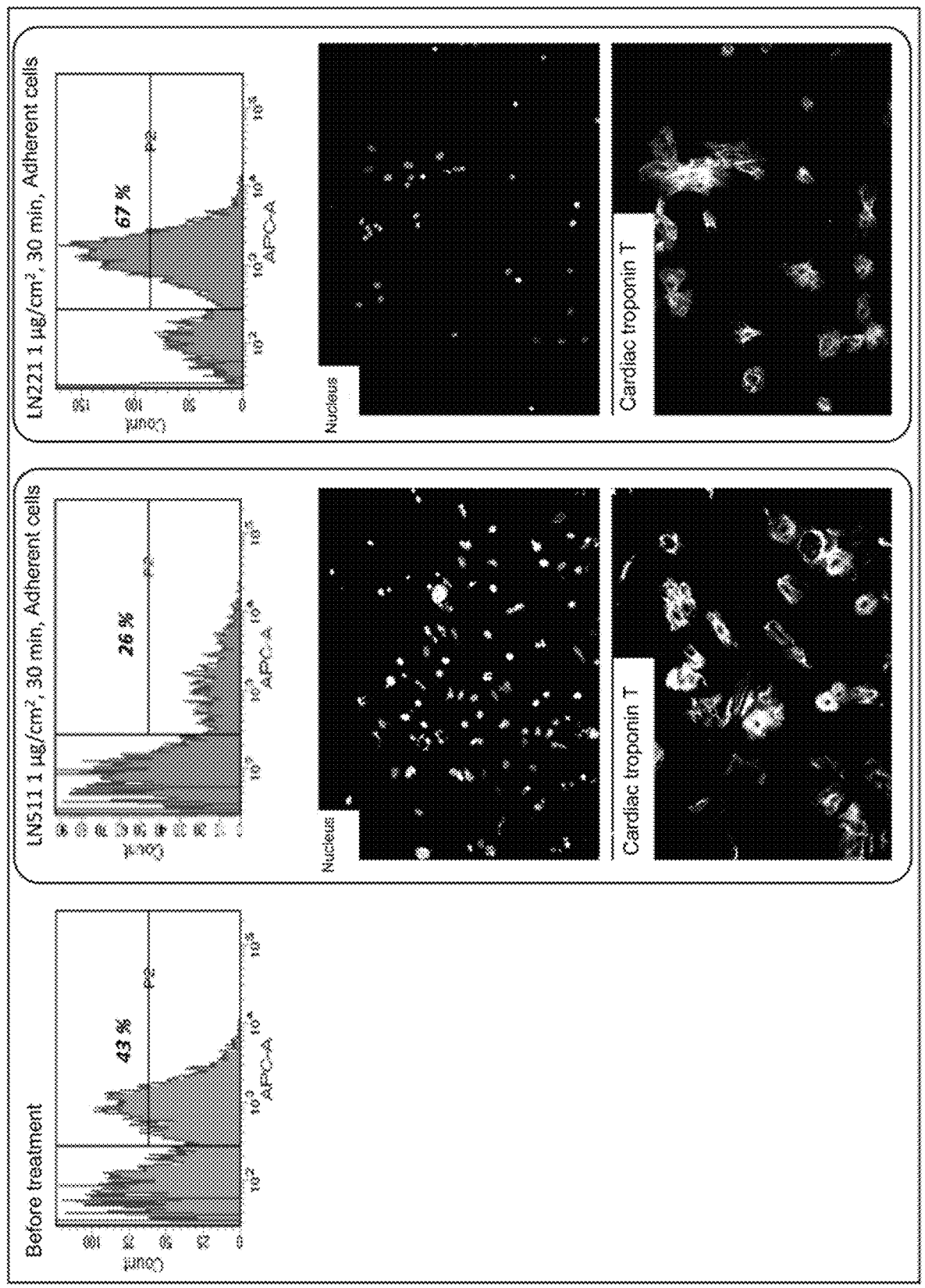
FIG. 8 shows the results of the comparison of the effects of 221E8 treatment and 511E8 treatment on the enrichment of cardiomyocytes in a cell population obtained by induced differentiation of human iPS cells into cardiomyocytes.

The results are shown in FIG. 8. The flow cytometry charts are shown in the upper row, the fluorescence microscopic images of nuclear staining are shown in the middle row, and the fluorescence microscopic images of cardiac troponin T-positive cells are shown in the lower row. As shown in FIG. 8, the percentage of cardiomyocytes before the treatment was 43%, but the percentage of cardiomyocytes in the adherent cells collected after the treatment with 511E8 was 26%, which was lower than the level before the treatment. On the other hand, the percentage of cardiomyocytes in the adherent cells collected after the treatment with laminin 221E8 was 67%, which was higher than the level before the treatment. When the adherent cells after the treatment with 511E8 or 221E8 were cultured, the number of nuclear stained cells in the case of the treatment with 221E8 was smaller than that in the case of the treatment with 511E8, but most of the nuclear stained cells in the former case were cardiac troponin T-positive cells. On the other hand, cells other than cardiac troponin T-positive cells were abundant in the case of the treatment with 511E8. These results show that the treatment with 221E8 is effective for enrichment of cardiomyocytes.

Example 9: Comparison of Effects of 221E8 Treatment and Glucose-Free Medium Treatment on Purification of Cardiomyocytes After the induced differentiation of the 253G1 cells into cardiomyocytes, that is, after the cells differentiated in a 16- to 18-day culture were collected according to the method described in section (3) of the above "Experimental Materials and Methods", the cells were divided into 2 aliquots. One aliquot was treated with glucose-free medium, and the other was treated with 221E8.

The treatment with glucose-free medium followed the method of Tohyama et al. (Shugo Tohyama et al., Cell Stem Cell, 12, 127-137, 2013). Specifically, after the induced differentiation, the resulting embryoid bodies were not pre-treated with trypsin-EDTA but directly cultured in glucose-free medium (i.e., glucose-free DMEM medium (Life Technologies)) supplemented with 4 mM lactic acid (Wako Pure Chemical Industries, Ltd.) for 6 days. As a control, the cells were cultured using a usual medium (DMEM containing 1% bovine serum albumin) instead of the glucose-free medium. The medium was replaced 3 hours after the onset of the culture, and replaced again 3 days after the onset of the culture. After the 6-day culture, the embryoid bodies were dissociated into cells with 0.05% trypsin-EDTA, and the cells were collected.

As a 221E8-treated group, the embryoid bodies after the induced differentiation were dissociated into cells with 0.05% trypsin-EDTA, and the cells were cultured on a plate coated with 1 μg/cm$^2$ 221E8. As a control, the cells were cultured on a plate coated with fetal bovine serum instead of 221E8. Three hours after the onset of the treatment, non-adherent cells were removed. After addition of a fresh medium, adherent cells were kept cultured on the plate, i.e., the plate coated with 1 μg/cm$^2$ 221E8 or the plate coated with fetal bovine serum, for 6 days. After 3 days of the culture, the medium was replaced. After the 6-day culture, the cells were collected by 0.05% trypsin-EDTA treatment.

The percentage of cardiac troponin T-positive cells (the percentage of cardiomyocytes) and the percentage of BC2LCN-positive cells (the percentage of undifferentiated cells) in the cells collected after the 6-day culture in each group were evaluated by flow cytometry.

Figure 9:
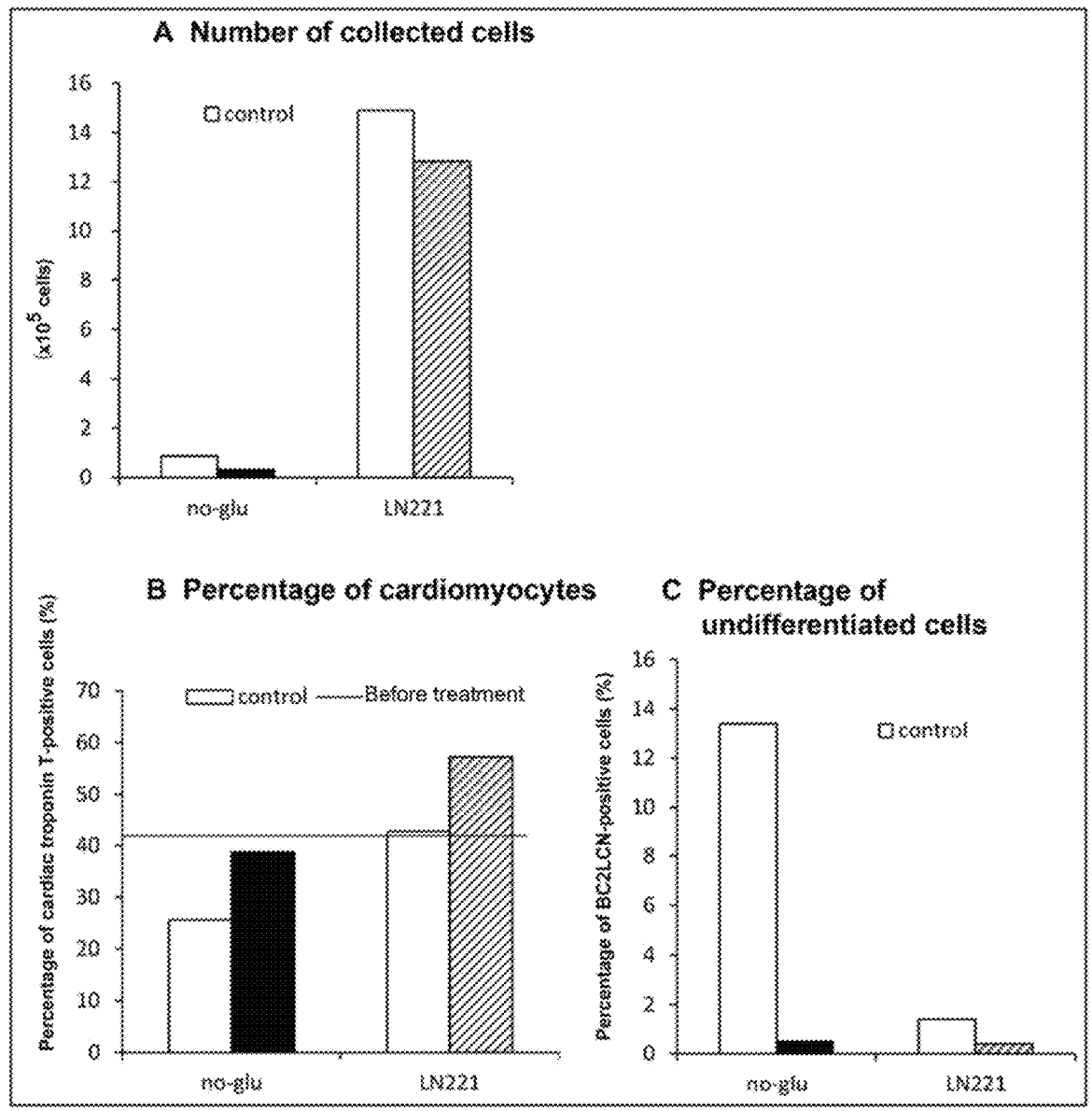
FIG. 9 shows the results of the comparison of the effects of 221E8 treatment and glucose-free medium treatment on the purification of cardiomyocytes in a cell population obtained by induced differentiation of human iPS cells into cardiomyocytes.

The results are shown in FIGS. 9A, 9B and 9C. FIG. 9A shows the number of the collected cells, FIG. 9B shows the percentage of cardiomyocytes, and FIG. 9C shows the percentage of undifferentiated cells. In the figures, the glucose-free medium, group (no-glu) is shown in black bars, the 221E8 treatment group is shown in hatched bars, and their control groups are shown in white bars.

As shown in FIG. 9A, the number of the collected cells was about 100,000 in the glucose-free medium group and in its control group, in both of which the embryoid bodies directly had been cultured, but the 221E8 treatment group and its control group, in both of which adhesion culture had been performed, showed a remarkably higher number of the collected cells, which was 1 million or more. These results show that the 221E8 treatment is less cytotoxic than the glucose-free medium treatment and is also effective for the maintenance of cardiomyocytes.

As shown in FIG. 9B, the percentage of cardiomyocytes before the treatment was 42.1% (represented by the horizontal line in the graph of FIG. 9B). The percentage of cardiomyocytes after the 6-day culture was 25.6% in the control group for the glucose-free medium culture (usual embryoid body culture), but the glucose-free medium group showed a higher percentage of cardiomyocytes, which was 38.7%. Meanwhile, the percentage of cardiomyocytes after the 6-day culture was 42.6% in the control group for the 221E8 treatment (usual adhesion culture), but the 221E8 treatment group showed a higher percentage of cardiomyocytes, which was 57.2%. The percentages of cardiomyocytes both in the glucose-free medium group and in the 221E8 treatment group were higher than those in the corresponding control groups, and in particular, the percentage of cardiomyocytes in the 221E8 treatment group was remarkably higher than that before the treatment.

As shown in FIG. 9C, the percentage of undifferentiated cells after the 6-day culture was 13.3% in the control group for the glucose-free medium, culture (usual embryoid body culture), but was 0.5% in the glucose-free medium group. Meanwhile, the percentage of undifferentiated cells after the 6-day culture was 1.4% in the control group for the 221E8 treatment (usual adhesion culture), but was 0.4% in the 221E8 treatment group. The relative degree of elimination of undifferentiated cells based on the percentage of undifferentiated cells in the control group was higher in the glucose-free medium treatment than that in the 221E8 treatment, but the percentage of undifferentiated cells after the treatment was 0.4% to 0.5% in both cases. Therefore, both the treatments were almost comparable in the viewpoint of the residual ratio of undifferentiated cells.

The above results reveal that the 221E8 treatment showed a considerably larger number of the collected cells than that in the glucose-free medium treatment, a remarkably higher percentage of cardiomyocytes than that before the treatment, and a percentage of undifferentiated cells comparable to that in the glucose-free medium treatment. Therefore, the 221E8 treatment was shown to be considerably more efficient for the purification of cardiomyocytes than the glucose-free medium treatment. That is, the present invention was shown to be superior to the method using glucose-free medium in purifying cardiomyocytes.

The present invention is not limited to the particular embodiments and examples described above, and various modifications can be made within the scope of the appended claims. Other embodiments provided by suitably combining technical means disclosed in separate embodiments of the present invention are also within the technical scope of the present invention. All the academic publications and patent literature cited in the description are incorporated herein by reference.

The invention claimed is:

1. A method for preparing a cardiomyocyte population for transplantation therapy, the method comprising the steps of: (1) inducing pluripotent mammalian stem cells to differentiate into cardiomyocytes, (2) bringing a cell population obtained in step (1) into contact with a laminin E8 fragment selected from the group consisting of laminin α2β1γ1 E8 fragment, laminin α2β2γ1E8 fragment, laminin α1β1γ1 E8 fragment and laminin α1β2γ1 E8 fragment, and (3) retrieving cardiomyocytes adherent to the laminin E8 fragment, wherein the cell population obtained in step (1) is heterogeneous containing differentiated cardiomyocytes and undifferentiated pluripotent mammalian stem cells, wherein the contact of the cell population with the laminin E8 fragment in step (2) is achieved by (a) adding a cell suspension containing the cell population obtained in step (1) to a culture vessel having a culture surface coated with the laminin E8 fragment at a coating concentration of 0.1 μg/cm$^2$ to 2 μg/cm$^2$, followed by incubation for 15 minutes to 180 minutes; (b) by adding a carrier coated with the laminin E8 fragment at a coating concentration of 0.1 μg/cm$^2$ to 2 μg/cm$^2$ to a cell suspension containing the cell population obtained in step (1), followed by incubation for 15 minutes to 180 minutes; or (c) by passing a cell suspension containing the cell population obtained in step (1) through a hollow fiber membrane having an inner surface coated with the laminin E8 fragment at a coating concentration of 0.1 μg/cm$^2$ to 2 μg/cm$^2$ for 15 minutes to 180 minutes, and wherein step (3) comprises removing undifferentiated pluripotent mammalian stem cells not adherent to the laminin E8 fragment and then detaching cardiomyocyte adherent to the laminin E8 fragment or wherein step (3) comprises removing undifferentiated pluripotent mammalian stem cells not adherent to the laminin E8 fragment and keeping cardiomyocytes adherent to the laminin E8 fragment as they are without detachment for continuous culture.

2. The method according to claim 1, further comprising, between steps (1) and (2), a step of eliminating the undifferentiated pluripotent mammalian stem cells from the cells population obtained in step (1), the step of eliminating undifferentiated pluripotent mammalian stem cells comprising the substeps of: (A) bringing the cell population obtained in step (1) into contact with a laminin E8 fragment having binding specificity to integrins expressed on the surface of undifferentiated pluripotent mammalian stem cells selected from the group consisting of laminin α5β1γ1 E8 fragment, laminin α5β2γ1 E8 fragment, laminin α3β1γ1 E8 fragment, laminin α3β2γ1 E8 fragment and laminin α3β3γ2 E8 fragment, and (B) retrieving cardiomyocytes not adherent to the laminin E8 fragment, wherein the contact of the cell population with the laminin E8 fragment in substep (A) is achieved by (a) adding a cell suspension containing the cell population obtained in step (1) to a culture vessel having a culture surface coated with the laminin E8 fragment at a coating concentration of 0.1 μg/cm$^2$ to 2 μg/cm$^2$, followed by incubation for 5 minutes to 30 minutes; (b) by adding a carrier coated with the laminin E8 fragment at a coating concentration of 0.1 μg/cm$^2$ to 2 μg/cm$^2$ to a cell suspension containing the cell population obtained in step (1), followed by incubation for 5 minutes to 30 minutes; or (c) by passing a cell suspension containing the cell population obtained in step (1) through a hollow fiber membrane having an inner surface coated with the laminin E8 fragment at a coating concentration of 0.1 μg/cm$^2$ to 2 μg/cm$^2$ for 5 minutes to 30 minutes, wherein substep (B) comprises collecting cardiomyocytes contained in a collected medium and in a wash solution collected after washing the coated surface.

3. A method for increasing the purity of cardiomyocytes in a cell population obtained by induced differentiation of pluripotent mammalian stem cells into cardiomyocytes, the method comprising step 1-1: inducing pluripotent mammalian stem cells to differentiate into cardiomyocytes, step 1-2: bringing the cell population obtained in step 1-1 into contact with a laminin E8 fragment selected from the group consisting of a laminin E8 fragment selected from the group consisting of laminin α2β1γ1 E8 fragment, laminin α2β2γ1 E8 fragment, laminin α1β1γ1 E8 fragment and laminin α1β2γ1 E8 fragment, and step 2: retrieving cardiomyocytes adherent to the laminin E8 fragment, wherein the cell population obtained in step 1-1 is heterogeneous containing differentiated cardiomyocytes and undifferentiated pluripotent mammalian stem cells, wherein the contact of the cell population with the laminin E8 fragment in step 1-2 is achieved by (a) adding a cell suspension containing the cell population obtained in step 1-1 to a culture vessel having a culture surface coated with the laminin E8 fragment at a coating concentration of 0.1 µg/cm$^2$ to 2 µg/cm$^2$, followed by incubation for 15 minutes to 180 minutes; (b) by adding a carrier coated with the laminin E8 fragment at a coating concentration of 0.1 µg/cm$^2$ to 2 µg/cm$^2$ to a cell suspension containing the cell population obtained in step 1-1, followed by incubation for 15 minutes to 180 minutes; or (c) by passing a cell suspension containing the cell population obtained in step 1-1 through a hollow fiber membrane having an inner surface coated with the laminin E8 fragment at a coating concentration of 0.1 µg/cm$^2$ to 2 µg/cm$^2$ for 15 minutes to 180 minutes, and wherein step 2 comprises removing undifferentiated pluripotent mammalian stem cells not adherent to the laminin E8 fragment and then detaching cardiomyocytes adherent to the laminin E8 fragment or wherein step 2 comprises removing undifferentiated pluripotent mammalian stem cells not adherent to the laminin E8 fragment and keeping cardiomyocytes adherent to the laminin E8 fragment as they are without detachment for continuous culture.

4. The method according to claim 3, further comprising, between steps 1-1 and step 1-2, a step of eliminating the undifferentiated pluripotent mammalian stem cells from the cell population obtained in step 1-1, the step of eliminating undifferentiated pluripotent mammalian stem cells comprising the substeps of: (A) bringing the cell population obtained in step 1-1 into contact with a laminin E8 fragment having binding specificity to integrins expressed on the surface of undifferentiated pluripotent mammalian stem cells selected from the group consisting of laminin α5β1γ1 E8 fragment, laminin α5β2γ1 E8 fragment, laminin α3β1γ1 E8 fragment, laminin α3β2γ1 E8 fragment and laminin α3β3γ2 E8 fragment, and (B) retrieving cardiomyocytes not adherent to the laminin E8 fragment, wherein the contact of the cell population with the laminin E8 fragment in substep (A) is achieved (a) by adding a cell suspension containing the cell population obtained in step 1-1 to a culture vessel having a culture surface coated with the laminin E8 fragment at a coating concentration of 0.1 µg/cm$^2$ to 2 µg/cm$^2$, followed by incubation for 5 minutes to 30 minutes; (b) by adding a carrier coated with the laminin E8 fragment at a coating concentration of 0.1 µg/cm$^2$ to 2 µg/cm$^2$ to a cell suspension containing the cell population obtained in step 1-1, followed by incubation for 5 minutes to 30 minutes; or (c) by passing a cell suspension containing the cell population obtained in step 1-1 through a hollow fiber membrane having an inner surface coated with the laminin E8 fragment at a coating concentration of 0.1 µg/cm$^2$ to 2 µg/cm$^2$ for 5 minutes to 30 minutes, and wherein substep (B) comprises collecting cardiomyocyte contained in a collected medium and in a wash solution collected after washing the coated surface.

* * * * *